(12) United States Patent
Handa et al.

(10) Patent No.: US 6,545,132 B1
(45) Date of Patent: Apr. 8, 2003

(54) MICROSPHERE CONTAINING GLYCIDYL METHACRYLATE COVERED POLYMER AND SPACER COUPLED COMPOUND FOR ISOLATING SUBSTANCES

(76) Inventors: Hiroshi Handa, 17-16, Sakurajosui 1-chome, Setagaya-ku, Tokyo (JP), 156; Haruma Kawaguchi, 86-43, Nakazawa-cho, Asahi-ku, Yokohama-shi, Kanagawa (JP), 241

( * ) Notice: Subject to any disclaimer, the term of this patent is extended or adjusted under 35 U.S.C. 154(b) by 0 days.

(21) Appl. No.: 09/440,597

(22) Filed: Nov. 15, 1999

Related U.S. Application Data

(63) Continuation-in-part of application No. 08/795,927, filed on Feb. 5, 1997, now Pat. No. 5,986,072.

(30) Foreign Application Priority Data

Feb. 5, 1996 (JP) ................................. 8-18827
Sep. 17, 1996 (JP) ............................... 8-266711

(51) Int. Cl.⁷ .......................... C07K 1/22; C07K 17/08; C07K 17/06; C12N 15/00; C12N 11/06
(52) U.S. Cl. ..................... 530/413; 435/711; 435/180; 435/181; 435/455; 435/803; 435/815; 530/326; 530/350; 530/815; 530/816
(58) Field of Search ................................. 530/413, 326, 530/350, 815, 816; 435/455, 180, 181, 803, 815, 4, 7.1

(56) References Cited

U.S. PATENT DOCUMENTS 5,122,600 A    6/1992   Kawaguchi et al. .......... 536/27
5,986,072 A  * 11/1999  Handa et al. ................ 530/413

OTHER PUBLICATIONS

J. Liu et al., *Cell*, 66:807–815 (1991).
S. O'Keefe et al., *Nature*, 357:692 (1992).
N. Clipstone et al., *Nature*, 357:695 (1992).
R. Handschumacher et al., *Science*, 226544 (1984).
J. Siekierka et al., *J. Immunol.*, 143:1580–1583 (1989).
T. Wada et al., *Methods in Enzymology*, 254:595–605 (1995).
Y. Inomata et al., *Analytical Biochemistry*, 206:109–114 (1992).
Y. Inomata et al., *Colloids and Surfaces B: Biointerfaces*, 4:231–241 (1995).
T. Shiroya et al., *IJBC*, 1:191–198 (1995).
Patent Abstracts of Japan, vol. 016, No. 568 (1992).
Patent Abstracts of Japan, vol. 012, No. 219 (1988).
Database WPI, Section Ch, Week 199213, Derwent Publications Ltd., London, GB; Class A96 AN 1992–102210 XP002144632.
Tanaka et al., *European Journal of Pharmacology, Molecular Pharmacology Section*, 291(2): 121–127 (1995).
Robson et al., Swissport Sequence Data Base, XP002144594 (1992).
Xanthoudakis et al., PIR2 Sequence Data Base, XP002144595 (1993).
Seki et al., PIR2 Sequence Data Base, XP002144596 (1992).

* cited by examiner

*Primary Examiner*—David M. Naff
(74) *Attorney, Agent, or Firm*—Peter F. Corless; Christine C. O'Day; Edwards & Angell, LLP

(57) ABSTRACT

A microsphere is prepared containing a compound possessing physiological activity coupled to a styrene-glycidyl methacrylate polymer through a spacer. Compounds that may be used include receptors such as proteins, and 3-[(5-(2,3-dimethoxy-6-methyl-benzoquinonyl)]-2-nonyl-2-propionic acid. A preferred spacer is an ethylene glycol diglycidyl ether derivative. Preferably, the whole surface of the styrene-glycidyl methacrylate polymer is covered with glycidyl methacrylate. The microsphere may be used for isolating and detecting substances such as proteins that bind to the coupled compound.

4 Claims, 15 Drawing Sheets

OC: Open Circular DNA
SC: Supercoiled DNA

OC: Open Circular DNA
SC: Supercoiled DNA

| | |
|---|---|
| 1 | Immobilize GST or GST - p50NH - KB on Glutathione Sepharose beads. |
| 2 | Mix each beads and His - Ref - 1. |
| 3 | Wash them by the buffer. |
| 4 | Elution by boiling. |
| 5 | Detect Ref - 1 carried on beads, by immunoblot method with anti - Ref - 1 antibody. |

His Ref - 1 ( ug ):        0.1          5          5

Ratio to input of bound Ref - 1          12.4%          0.4%

MICROSPHERE CONTAINING GLYCIDYL METHACRYLATE COVERED POLYMER AND SPACER COUPLED COMPOUND FOR ISOLATING SUBSTANCES

This application is a continuation-in-part of application Ser. No. 08/795,927, filed Feb. 5, 1997, now U.S. Pat. No. 5,986,072.

BACKGROUND OF THE INVENTION

1. Field of the Invention

The present invention relates to a microsphere which is prepared by coupling a substance possessing physiological activities to a styrene-glycidyl methacrylate polymer through a spacer as well as a process of isolating an objective or targeted substance by using the microsphere of the invention.

2. Background

Cells constituting a living body are exposed to various kinds of stimulation from the external environment all the time. To respond to such stimulation the cells lead some gene groups to expression. As a result, various living phenomena can occur, such as induction of cell growth and/or cell differentiation and maintenance of physiological homeostasis. Extracellular stimulation is transformed into an intracellular signal, which activates a specific proteinous transcription factor. The functionally activated transcription factor binds to a specific base sequence on a chromosome to induce a gene group under its regulation to expression. The product of the induced gene expression primarily functions to respond to the stimulation in some cases. In the other cases, the product of the induced gene expression further activates another transcription factor that induces another gene group under its regulation to expression to secondarily respond to the stimulation. In either case, cellular response to the stimulation from the external environment is concluded to be functional transformation of transcription factors.

In recent years, an extremely interesting fact was revealed. That is, mechanisms of action of cyclosporin A (CysA) and FK506, immunosuppressive drugs, have been revealed. See J. Lin et al., *Cell*, 66:807–815 (1991); S. J. O'Keefe et al., *Nature*, 357:692 (1992); and N. A. Clipstone et al., *Nature*, 357:695 (1992). The first opportunity for revealing the mechanisms is the identification of intracellular receptors to these drugs. See R. E. Handschumacher et al., *Science*, 226, 554; and J. J. Sekierka et al., *J. Immunol.*, 143:1580–1583 (1989). On the basis of these findings, a series of signaling pathway following stimulation by antigen was revealed in T-cell that is immunocompetent cell.

Accordingly, investigation and identification of intracellular receptors to drugs, as well as elucidation of signaling pathway, are expected to be further developed into developmental research of new drugs targeting the signaling pathway and research for novel drug designs.

Conventional methods of isolation and purification of intracellular receptors to drugs are fractionation of crude cell extracts by using various columns, followed by detection of factors binding to labeled drugs in each fraction. Therefore, two steps of procedure, the first one was isolation and purification using columns and the second one was assay for binding activity against drugs, have been necessarily performed until now.

Accordingly, for the purpose of purification, identification and functional analysis of receptors to a specific drug, located within cells or on cellular membrane, certain drug-immobilized microspheres have been designed and constituted.

SUMMARY OF THE INVENTION

According to the conventional methods of purification, it can take an exceedingly long time to purify drug-binding factors from crude cell extracts and moreover, a yield of factors is quite low due to repeated fractionation using various columns. Therefore, a huge amount of starting material is necessary for the determination of an amino acid sequence of drug-binding factors. It also can be most difficult to establish an assay method for binding activity of receptors against drugs because obtained drug receptors are usually not identified. Conventional methods of determination of binding of receptors to drugs are filter binding method and gel filtration method which utilize the fact that drug receptors (proteins) bind to filters and that sizes of drugs binding to receptors become larger than free drugs and receptors. However, some receptors that do not bind to filters or other receptors change their conformation after binding to filters and discharge drugs. Therefore, properties of drug receptors should be preliminarily investigated in the conventional methods. The present invention aims at solving the above mentioned problems to provide drug-immobilized particles and a process of purifying proteins.

According to the present invention, a microsphere comprising styrene-glycidyl methacrylate polymer is provided, and isolation, purification and identification of receptors to a specific compound possessing physiological activities are easily performed.

In addition, the present invention is concerned with microspheres prepared by coupling substances and proteins purified using the microspheres of the invention.

The present invention is further concerned with microspheres comprising a substance possessing physiological activity, a polymer and a spacer, wherein at least one functional group of any of the substance possessing physiological activity, the polymer or spacer is converted to another type of functional group. The present invention also relates to a process of preparing such microspheres.

DETAILED DESCRIPTION OF THE INVENTION

Figure 1:
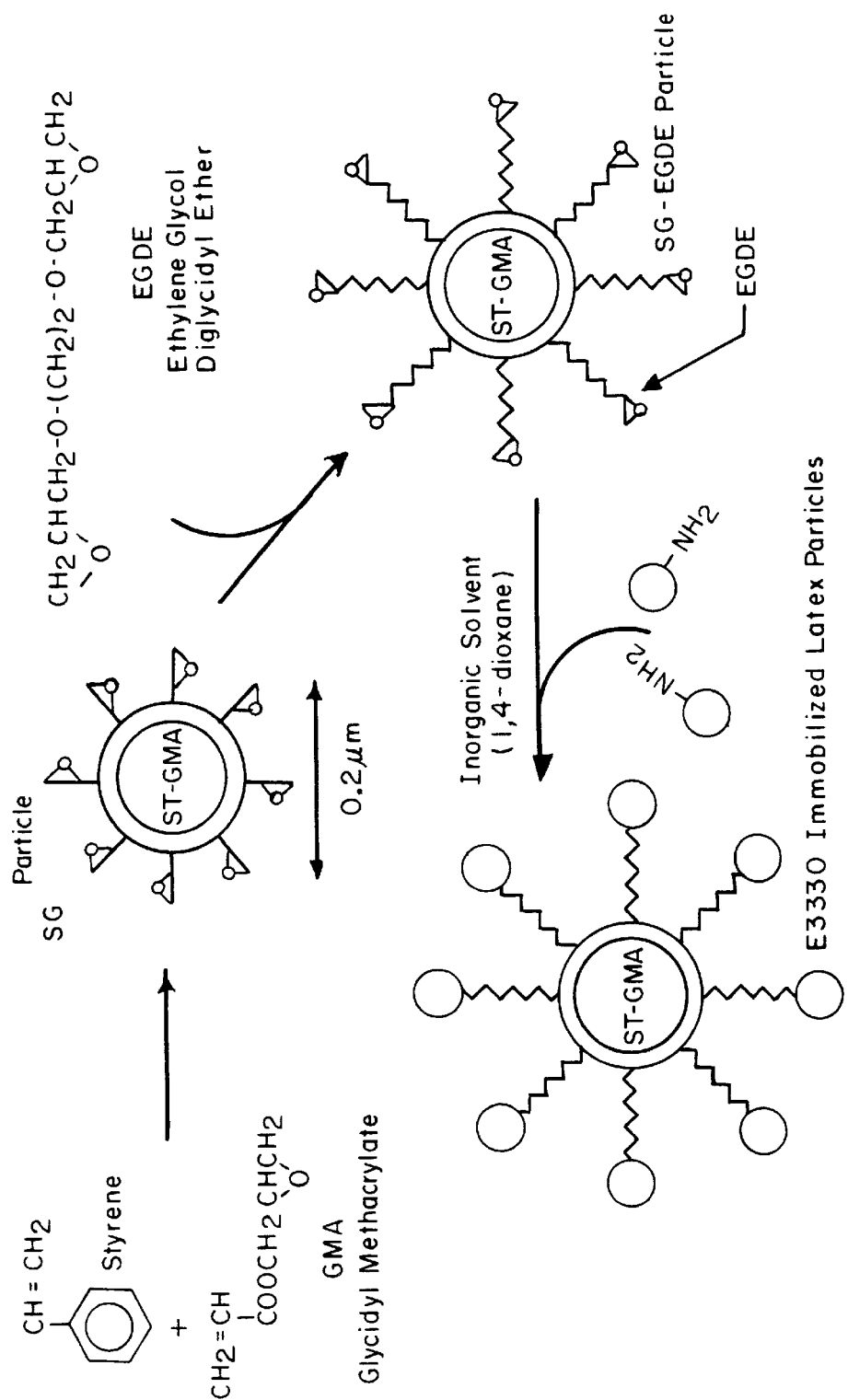
FIG. 1 is a schematic for the preparation method of a styrene-glycidyl methacrylate polymer and a styrene-glycidyl methacrylate polymer connected with a spacer.

The present invention provides a microsphere prepared by coupling a compound possessing physiological activity to a styrene-glycidyl methacrylate polymer through a spacer. In addition, the present invention provides a process of isolating a substance by using a microsphere prepared by coupling a compound possessing physiological activities to a styrene-glycidyl methacrylate polymer through a spacer.

More particularly, the present invention is concerned with a process of isolating an objective substance that can adhere to a substance possessing physiological activities from a mixture containing the objective substance by using a microsphere prepared by coupling the substance possessing physiological activities to a styrene-glycidyl methacrylate polymer through a spacer. In more detail, the process of isolating a substance according to the present invention includes mixing crude cell extracts and microspheres prepared by coupling compounds possessing physiological activity to styrene-glycidyl methacrylate polymers through spacers, followed by isolation of microspheres, and then, eluting the objective substance adhering to the substances possessing physiological activities on the microspheres, to provide a useful process of isolating an objective or targeted substance.

The present invention also provides with proteins isolated according to the above procedure. In addition, the present invention provides peptides or proteins comprising active moieties of isolated proteins as receptors.

As the substance forming particles of microspheres in the present invention, styrene-glycidyl methacrylate polymers are employed. There is no special restriction on their states of polymerization or morphological properties in the preparation method in which formed particles should be isolated from a liquid phase. However, it is preferable that particles are prepared by soap-free emulsion polymerization according to the method developed by Inomata et al. such as described in Y. Inomata et al., Anal. Biochem., 206:109 (1992).

The spacer in the present invention is a chemical compound interposed between the above particle and a compound possessing physiological activity as discussed in more detail herein. A preferable spacer is a compound possessing one or more functional groups, such as an amino group, carboxyl group and epoxy group, on both its ends before binding to a particle and a substance possessing physiological activity. As for the selection of a spacer in the present invention, there is no special restriction but the spacer should be a substance connecting the above styrene-glycidyl methacrylate polymer with a substance possessing physiological activities at an appropriate distance. A particularly preferred spacer is an ethylene glycol diglycidyl ether derivative.

As for the selection of a substance possessing physiological activity (which will be occasionally abbreviated as physiologically active substance, hereinafter) in the present invention, there is no special restriction but the substance should possess activity in a living body and interaction and/or affinity to another substance of intra- or extra-living body. It is further preferable to employ a compound that specifically binds to a receptor located within cells or on cellular membrane. In a case where the substance possessing physiological activity has functional groups connectable with the above spacer in its molecular structure, such as amino group and hydroxyl group, the functional group is utilized as a group connected with a spacer. In the other case where the substance possessing physiological activity has no functional group connectable with the above spacer in its molecular structure, a functional group connectable with the above spacer is additionally induced into the concerned physiologically active substance and then, it is connected with a spacer. In either case it is necessary to pay attention not to inactivate physiological activity of the concerned physiologically active substance by connecting the physiologically active substance with a spacer. Namely, it is important to confirm that an objective or desired physiological activity is not inactivated by connecting the physiological active substance with a spacer.

As the substance possessing physiological activities in the present invention, for example, a 3-[(5-(2,3-dimethoxy-6-methyl-1,4-benzoquinonyl))]-2-nonyl-2-propionic acid (which will be occasionally abbreviated as E3330, hereinafter or derivative thereof) may be suitably employed. Other examples of substances possessing physiological activity useful in the microspheres of the present invention include DM852, H-9, DQ2511 and KF49389.

A preparation method of a microsphere consisting of a compound possessing physiological activities coupled to a styrene-glycidyl methacrylate polymer through a spacer according to the present invention is as follows. A particle composed of a styrene-glycidyl methacrylate polymer (which will be occasionally abbreviated as a SG-particle, hereinafter) is prepared according to an ordinary method. However, for the purpose of the SG-particle easily binding to a spacer, it is especially preferable to prepare a particle with a functional glycidyl group projecting on its surface and then, the glycidyl group on the SG-particle is ring-opened with appropriate reagents, such as ammonium hydroxide, followed by induction of a preferable functional group for binding to a spacer, depending on necessity. Subsequently, a spacer is bound to the SG-particle, followed by reaction with a substance possessing physiological activities or its derivatives. Thus, a microsphere of the present invention is prepared.

In these reactions, various solvents, such as dioxane, DMSO and water, are suitably employed, depending on necessity.

Figure 13:
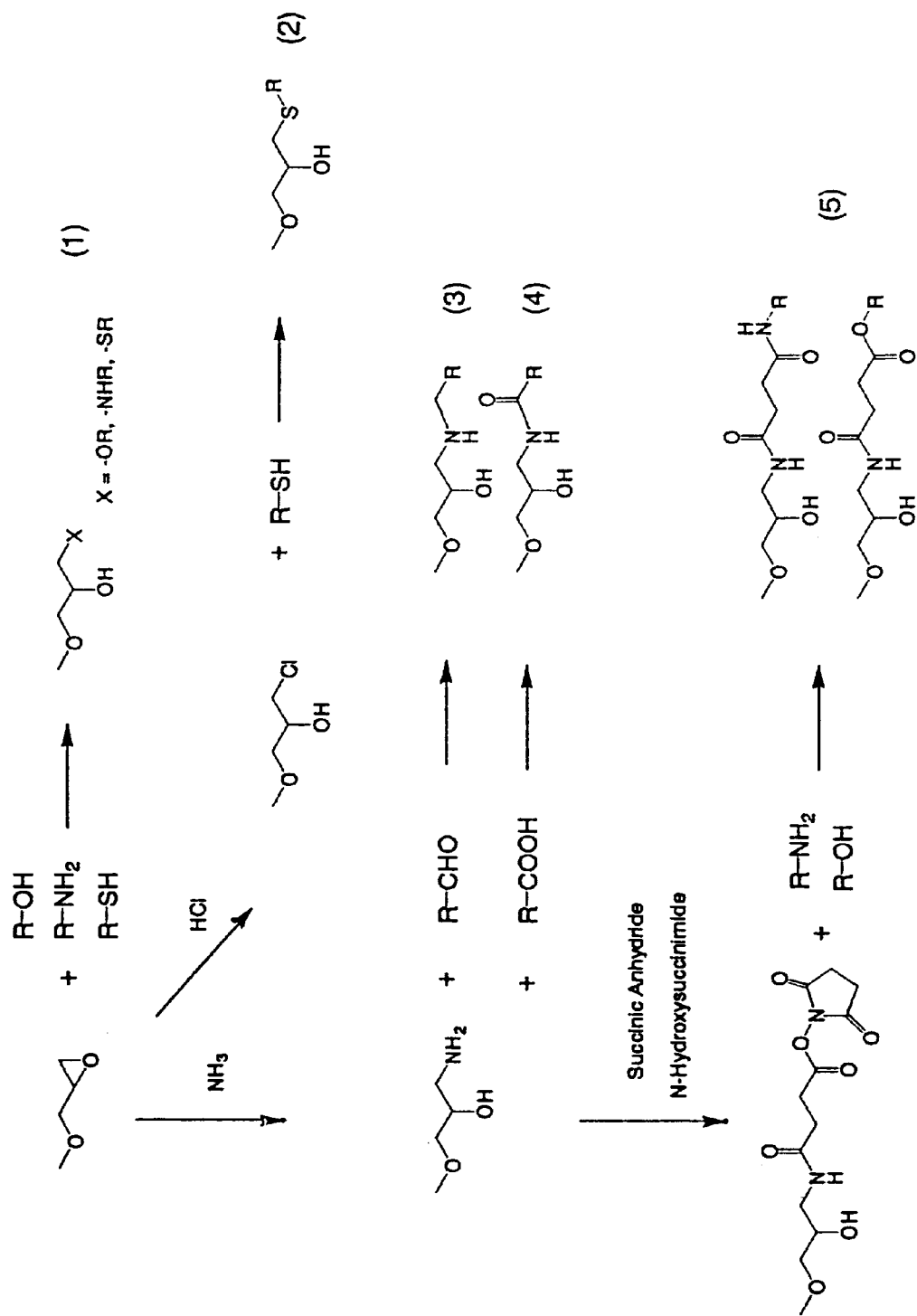
FIG. 13 shows reaction schemes for the conversion of epoxy groups to other chemical groups.

In certain embodiments of the present invention, the functional groups on the components of the microsphere of the present invention, i.e., particle, spacer or physiologically active substances, are converted to other types of groups having reactive carbons. For example, FIG. 13 shows the conversion of epoxide groups to other chemical groups useful for in the present invention. For the purposes of illustration, conversion of epoxide groups will be discussed.

Epoxide groups on any of the spacer, particle or physiologically active substances can be converted to another type of functional group. For example, an epoxide group can be covalently bound to a nucleophilic group such as hydroxy, amino and thiol group (reaction 1 in FIG. 13). In another embodiment, the epoxide group is treated with hydrochloric acid to introduce alkyl chloride to the surface of the particle or the end of the spacer. The chloride group can be substituted for a relatively strong nucleophile, such as thiol group (FIG. 13, reaction 2). This reaction is useful for selective incorporation of substances containing free thiol group. The chloride group can be replaced by a good leaving group, such as a p-toluenesulfonyl group, which enables the reaction with weak nucleophilic groups.

In another example, the epoxide group is treated with ammonium, which enables the introduction of an amino group on the particle or on the spacer. This amino group covalently binds to aldehyde groups via Schiff base. formation, and following reduction of the reaction site results in formation of a stable bond. (Reaction 3, FIG. 13). In yet another example, the amino group covalently binds to a carboxyl group by using a general coupling reagent for amide bond formation (reaction 4, FIG. 13). In yet another example, a carboxyl group is introduced by reacting succinic anhydride with the amino group. The generated carboxyl group reacts with a hydroxy group or amino group by using a coupling reagent, such as N-hydroxysuccinimide, to form a stable ester bond or amide bond respectively (reaction 5).

These methods are useful in converting at least one functional group on the particle, spacer, or physiologically active substances into other types of activated groups. These resulting groups can then react with other components to form the microspheres of the present invention. For example, the epoxide group on glycidylmethacrylate, one of components of the preferred particles, is converted into other types of activated groups. Similarly, ethylenediglycidylether, one preferred spacer has an epoxide group at both ends. Either one, or both of these epoxides can be converted into other activated groups. These converted groups are used to covalently bind to chemical groups, e.g., hydroxy, amino, thiol, aldehyde and/or carboxyl group contained in physiologically activated substances.

FIG. 1 shows an example for the preparation of a microsphere of the present invention. Appropriate compounds, such as styrene and glycidyl methacrylate, are polymerized according to an ordinary method, such as emulsion polymerization, to prepare a SG-particle with a functional glycidyl group projecting on its surface. Sizes of particles are selectively varied according to circumstances. However, the sizes (lengths) are ordinarily about 0.05 to 0.5 $\mu$m and preferably they are about 0.1 to 0.3 $\mu$m. The prepared SG-particle is reacted with a compound employed as a spacer, such as ethylene glycol diglycidyl ether (EDGE), to bind a spacer to the SG-particle. Thus, a spacer-binding SG-particle (SG-EGDE particle) is obtained. Then, the obtained particle is reacted with a physiological active substance possessing a reactive functional group, such as amino group, preferably in an organic solvent, such as dioxane. Thereby, a microsphere of the present invention, that is a physiologically active substance-immobilized latex particle, is prepared.

As for the selection of a mixture containing an objective substance for isolation according to the present invention, there is no special restriction but the mixture should contain a substance possessing an affinity and selective binding ability to a physiologically active substance employed in the preparation of a microsphere. It is ordinarily preferable that cell extracts, especially the cell extracts from the concerned physiological active substance-acting sites are employed as a mixture.

The isolation procedure in the present invention is conducted as follows. Physiologically active substance-binding microspheres and a mixture containing proteins, such as cell extracts, are mixed and stirred, if necessary, for several minutes to several hours. The microspheres to which proteins are adhering are separated and rinsed with a buffer solution, if necessary. Then, adhering proteins are eluted from the microspheres by using an appropriate solution, such as a potassium chloride solution, to be dissociated. Thus, the isolation procedure is conducted. There is no special restriction on the states of adhering conditions of an objective substance for isolation to a physiological active substance employed in the preparation of a microsphere. Any kinds of adhering, such as chemical bond (hydrogen bond, etc.) and chemical or physical adsorption, may be suitably employed.

Figure 2:
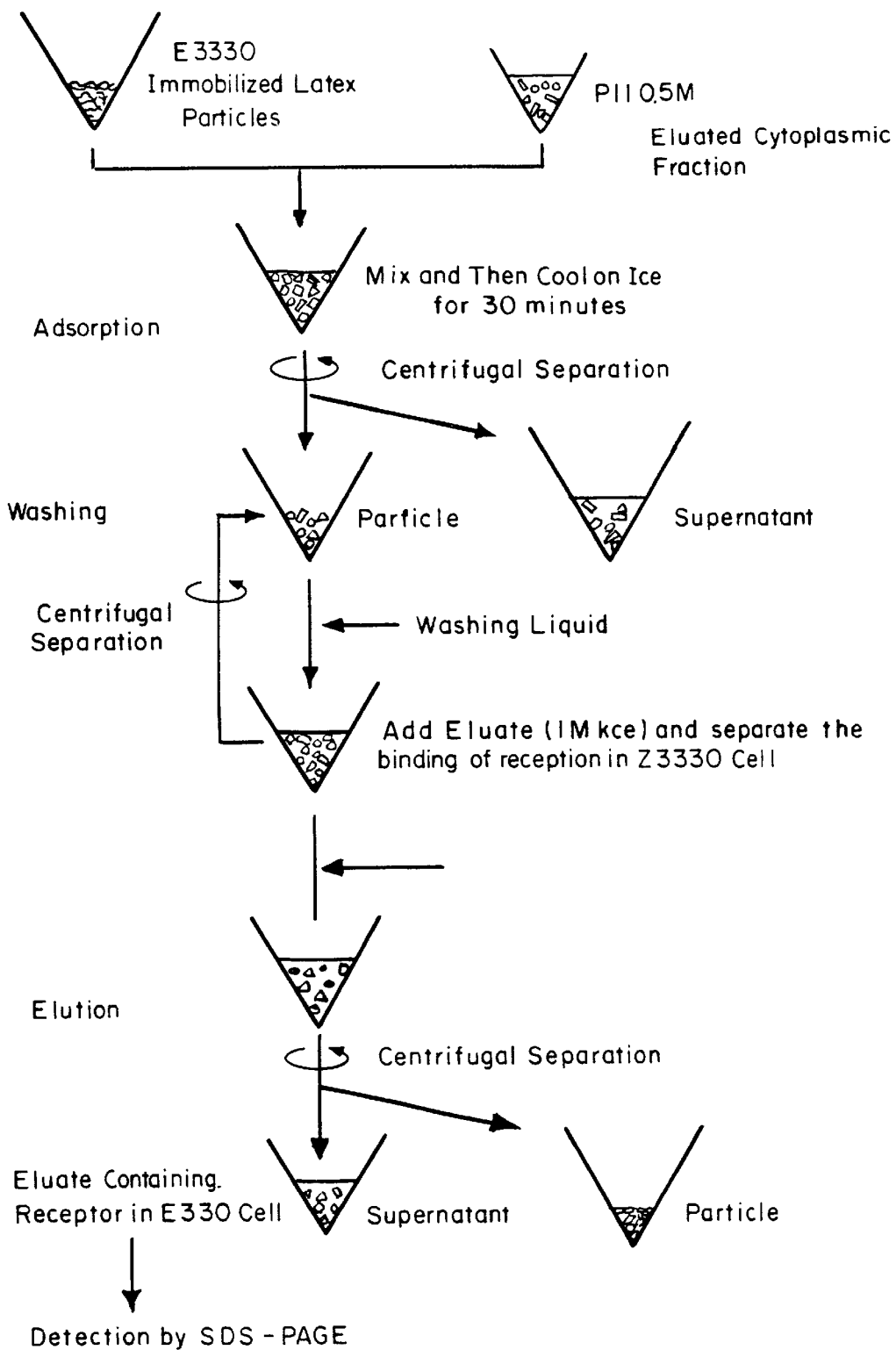
FIG. 2 is a schematic for the isolation method of a protein using microspheres of the present invention.

FIG. 2 shows an example for the isolation of a protein in the present invention. In this example, E3330 is employed as a physiologically active substance.

An obtained protein is detected by using SDS-PAGE or other suitable method. In addition, an obtained protein is purified according to an ordinary method, such as chromatography, if necessary.

Proteins isolated according to a process of the present invention are considered to be receptors to the physiologically active substance of microspheres. However, proteins isolated according to a process in the present invention are not limited to the receptors to the physiological active substance employed in the preparation of microspheres. Any kinds of substances possessing chemical, physical or biological affinities to the physiological active substance employed in the preparation of microspheres are able to be isolated according to a process in the present invention.

An obtained protein is purified, if necessary, and can be subjected to determination of its amino acid sequence. In addition, genes coding the concerned protein can be cloned according to an ordinary biotechnological procedure, and their base sequences can be determined. Furthermore, according to an ordinary genetechnology procedure, proteins or peptides composed of partial amino acid sequences of the concerned protein are expressed and an active moiety of the receptor protein can be determined. These procedures are also described in the working examples which follow, giving examples in which E3330 is employed as a physiologically active substance.

Structures of obtained receptors or domains composed of active moieties of the receptors can be elucidated through NMR analysis, x-ray crystal analysis or simulation analysis using computers on the basis of their amino acid sequences. For example, the protein, Ref-1, which is isolated according to a process of the present invention in which E3330 is employed as a physiologically active substance in the preparation of microspheres, is suggested to possess such structures as β-sheet/(α-helix/β-sheet in the domain of 82 a.a. to 106 a.a. through the above structural analyses. The amino sequence of Ref-1 (SEQ ID NO:4) is set forth in Example 9 which follows. Regions of 72 to 88 amino acid residues (SEQ ID NO:13) of Ref-1 are of particular interest and set forth in Example 14 which follows.

Further, peptides of the invention which have a sequence that is partially deleted, added or substituted with respect to SEQ ID NO:4 (which sequence is set forth in Example 9 which follows), and such peptides preferably comprise at least about 10 amino acids, more preferably at least about 15 to 50 amino acids, still more preferably at least about 40 to about 100 amino acids. Such peptides preferably have at least about 70 percent homology (sequence identity) to SEQ ID NO:4, more preferably at least about 80 or 90 percent sequence homology to SEQ ID NO:4. Also, such preferred peptides preferably will contain a region that has substantial sequence identity (e.g. about 80, 90 or 95 percent or more sequence identity) to SEQ ID NO:13 (which sequence is set forth in Example 14 which follows).

On the basis of the results of such stereochemical structural analyses and genetic analyses, one can readily determine which amino acid residue binds to a physiologically active substance employed in the preparation of microspheres among amino acids of the proteins or active moieties isolated according to a process of the present invention. In addition, one can investigate the interaction between the concerned physiologically active substance employed in the preparation of microspheres and amino acids of the isolated protein at molecular and/or atomic levels. Furthermore, it will be practicable to analyze chemical kinetics of the binding reactions. Many findings obtained from the above studies will not only identify the protein that is the receptor to the physiologically active substance employed in the preparation of microspheres but also reveal the mechanism of action of the concerned physiologically active substance in a living body. Moreover, it will be practicable to conduct a novel drug design by accurately controlling a new drug at an atomic level, of which binding mechanism is different from that of the physiological active substance employed in the preparation of microspheres concerning the interaction with the protein of the receptor. Various drugs designed according to the above method reasonably possess different functions from those of the physiological active substance employed in the preparation of microspheres. Therefore, the drugs will be utilized more properly for various purposes. Thus, a process in the present invention is extremely important for a novel procedure of the drug designs.

In addition, the present invention provides a process for isolation and detection of substances possessing affinities to a receptor by employing a protein with an ability of the concerned receptor as a substance possessing physiological activity coupled with microspheres. As a substance with an ability of a receptor, a whole protein of the receptor may be employed, but it is preferable to employ a domain that is obtained by trimming the receptor protein to an active domain of several tens (e.g. about 20 to 60) of amino acid residues as an active moiety of the concerned receptor.

Therefore, screening examinations on drugs specifically binding to the concerned receptor or its active domain will be practicably performed, according to the above methods. Thus, chemical synthetic substances expected to be useful drugs are easily isolated and detected among various drug libraries by conducting the screening examinations. The substance isolated and detected through the above screening examinations should possess affinities to the protein with an ability of a receptor coupled with microspheres. Therefore, the substance will be developed to be an effective ingredient of a medicine for promotion or inhibition of the activity of the concerned receptor.

According to the present invention, a microsphere composed of styrene-glycidyl methacrylate polymer is provided, and purification and identification of receptors to a specific compound possessing physiological activities, located within cells or on cellular membrane, are easily performed. Particles coupled with a substance possessing physiological activities specified in the present invention provide epoch-making and significant effects, that is, isolation and purification of a receptor to a drug are able to be conducted simultaneously with the evaluation on its binding activity to the drug, time required for isolation and purification of drugs is remarkably shortened and a recovery ratio is extremely improved, and investigation on the assay method for binding activity against a drug is not necessarily performed anymore. In addition, the present invention provides that an intracellular receptor to a drug or a compound can be isolated and purified by using the drug- or the compound-immobilized particles and then a structure and functions of the receptor can be determined. Furthermore, the present invention is indicated to be extremely useful for the development of novel drugs with superior functions on the basis of many findings obtained from the structural and functional analyses on receptors to drugs according to a process in the present invention.

All documents mentioned herein are incorporated herein by reference. The present invention is further illustrated by the following Examples. These Examples are provided to aid in the understanding of the invention and are not to be construed as limitations thereof.

EXAMPLE 1

(Preparation of Styrene-glycidyl Methacrylate Polymers)

Styrene (St; Wako Pure Chemicals. It was used after distillation under reduced pressure of 21.5 mmHg at 46° C.), glycidyl methacrylate (GMA; Wako Pure Chemicals. It was used after distillation under reduced pressure of 2 mmHg at 33° C.), divinyl-benzene (DVB; Tokyo Kasei), 2,2'-azobis (2-amidinopropane dihydrochloride) (V-50; Wako Pure Chemicals) and water were used in the following compositional formula: St/GMA/DVB/V-50/$H_2O$=1.2/1.8+0.3/0.04/0.06/110 (g)

After substituting a nitrogen gas in the mixture, reaction of polymerization was conducted at 70° C. for 24 hours. To polymerize the mixture soap-free emulsion polymerization was conducted according to the method developed by Inomata et al. (Y. Inomata et al., *Anal. Biochem.*, 206:109 (1992)).

Two hours after the initiation of polymerization, 0.3 g of GMA was added to the mixture to thoroughly cover the whole surface of the obtained polymers with GMA. The obtained polymers (SG-particles) were settled by centrifugation (15,000 rpm for 15 minutes at 4° C.), followed by decantation, and then re-suspended in 200 ml of water. The above procedure was repeated three times to wash the SG particles and finally suspended in water.

In order to induce amino groups into the washed SG-particles (0.25 g), $NH_4OH$ (55.3 mmol; corresponding to fifty times larger amount of GMA unit) was added to the particles, followed by adjustment of the pH value to 11 with 1N HCl. The mixture was stirred using a stirrer at 70° C. for 24 hours so that the epoxy group of GMA was ring-opened.

EXAMPLE 2

(Immobilization of a Spacer)

Next, an example for immobilization of ethylene glycol diglycidyl ether (EGDE; Wako Pure Chemicals), which was employed as a spacer, onto SG-particles obtained in the working example 1 is shown in the following.

An excess amount of EGDE, that was hundred times larger amount (mol) of amino groups on the surface of about 62.5 mg of SG-particles prepared in Example 1 above, was added to the SG-particles and then, the mixture was stirred at 30° C. for 24 hours at pH 11 (adjusted with 1N NaOH) so that an epoxy group of EGDE was covalently bound to an amino group on the surface of SG-particle. In order to avoid simultaneous immobilization of two epoxy groups at the both ends of an EGDE molecule onto SG-particles, such an excess amount of EGDE was added. Under these reaction conditions about 1 mmol of EGDE was immobilized onto 1 g of the particles. After the reaction was finished, the SG-particles were washed three times with water through a centrifugation procedure. Thus the obtained spacer-immobilized particles, that are SG-EGDE particles, were used for the particles to which a physiologically active compound is immobilized.

EXAMPLE 3

(Immobilization of an Amino Derivative of E3330 with a Spacer)

(a) (Induction of an amino group into E3330)

As E3330 does not possess an appropriate functional group, it is difficult to immobilize E3330 onto SG-EGDE particles. Therefore, $NH_2$-E3330 was synthesized through the induction of an amino group into E3330.

(b) (Confirmation of the functions of $NH_2$-E3330)

The functions of $NH_2$-E3330 were compared with those of E3330 with respect to transcriptional activation abilities of NF-$_K$B. In order to examine their functions transfection experiments were conducted by inducing the recombinant plasmid DNA possessing luciferase genes regulated by NF-$_K$B into Jurkat cells. As a result, it was ascertained that $NH_2$-E3330 reduced not so strongly as E3330 but certainly reduced the transcriptional activation abilities of NF-$_K$B. Thus, it was confirmed that the amino group induced into E3330 did not inhibit the binding of E3330 to intracellular receptors.

(c) (Immobilization of $NH_2$-E3330 to SG-EGDE particles)

Ten mg of SG-EGDE particles obtained in the working Example 2 above was washed three times with 1 ml of 1,4-dioxane through a centrifugation procedure. After washing, 500 μl of 1,4-dioxane solution containing 10 μmol of $NH_2$-E3330 was added to the packed SG-EGDE particles to disperse the SG-EGDE particles in the above solution, followed by reaction at 37° C. for 24 hours, in order to immobilize $NH_2$-E3330 to epoxy groups of EGDE on the surfaces of SG-EGDE particles. After the reaction was finished, the particles were washed three times with 20 μl of 1,4-dioxane through a centrifugation procedure. Then, the particles were dispersed in 1 ml of 1M Tris-HCl buffer solution (pH 7.4), allowed to be standing still at 4° C. for at least 24 hours and used, in order to thoroughly mask the intact epoxy groups on the surfaces of SG-EGDE particles. The drug-immobilized particles were stored at 4° C. in a dark place. The centrifugation procedure for washing was conducted at 15,000×g for 5 minutes at room temperature. Under these reaction conditions about 0.15 mmol of $NH_2$-E3330 was immobilized onto 1 g of the SG-EGDE particles. The above immobilized amount of $NH_2$-E3330 was obtained by subtracting the amount of $NH_2$-E3330 not bound to the SG-EGDE particles from the starting amount of $NH_2$-E3330. $NH_2$-E3330 shows the maximum absorption at the wavelength of 254.5 nm, so that each amount of $NH_2$-E3330 can be determined by measuring an absorbance at the wavelength of 254.5 nm on each sample, such as the starting solution, not-binding fraction and washing fractions. The measurement on the absorbance was conducted with DU-64 Spectrophotometer (BECKMAN).

EXAMPLE 4

(Preparation of a Crude Nuclear Extract and a Cytoplasmic Fraction)

The culture medium suspension of Jurkat cells ($2 \times 10^{10}$ cells), which were cultured in a suspension scale of 8 liters, was centrifuged using 500-ml-centrifugation tubes (NARGEN) at 500×g for 10 minutes at 4° C. for the purpose of collecting the cells. The collected cells were washed two times with PBS(−). The washing procedure was conducted using 50-ml-centrifugation tubes and the centrifugation conditions were at 700×g for 5 minutes at 4° C. Then, the final packed cell volume (PCV) was measured. Buffer A (10 mM Hepes pH 7.9, 1.5 mM $MgCl_2$, 10 mM KCl, 0.5 mM DTT), four times larger volume of the PCV, was added to the packed cells to suspend the cells. The cell suspension was allowed to stand still on ice for 20 minutes so that the cells were swollen. The cell membranes of the swollen cells were broken by 20 strokes using a 40-ml-B-type Dounce homogenizer (WHEATON), transferred to a 50-ml-centrifugation tube (NARGEN) and centrifuged at 4,200×g for 6 minutes at 4° C. for the purpose of separating a nuclear fraction (pellet) from a cytoplasmic fraction (supernatant).

Buffer A, five times larger volume of the PCV, was added to the isolated nuclear fraction to re-suspend the nuclei. The nuclear suspension was centrifuged at 4,200×g for 6 minutes at 4° C. for the purpose of removing the contaminated cytoplasmic fraction. The obtained nuclear pellet was dispersed in Buffer C (20 mM Hepes pH 7.9, 25% (v/v) glycerol, 0.42 M NaCl, 1.5 mM $MgCl_2$, 0.2 mM EDTA, 0.5 mM PMSF, 1 mM DTT), the same volume as the PCV, and thoroughly suspended by 10 strokes using a B-type Dounce homogenizer. The suspension was slowly stirred for 30 minutes at 4° C. for the purpose of extracting nuclear components. The extract was transferred to a 50-ml-centrifugation tube and centrifuged at 16,000×g for 30 minutes at 4° C. The obtained supernatant was dialyzed two times against one liter of Buffer D (20 mM Hepes pH 7.9, 20% (v/v) glycerol, 0.1 M KCl, 0.2 mM EDTA, 0.5 mM PMSF, 1 mM DTT) for 2.5 hours at 4° C.

On the other hand, the cytoplasmic fraction was transferred to another 50-ml-centrifugation tube and centrifuged again at 4,200×g for 6 minutes at 4° C. The obtained supernatant was transferred to an ultra-centrifugation tube (BECKMAN: No. 355620) and ultracentrifuged at 35 Krpm for one hour at 4° C. (BECKMAN: Rotor Type 35). The obtained supernatant was dialyzed in the same manner as the above procedure for the nuclear extract.

After the completion of the dialyses, the nuclear extract and the cytoplasmic fraction were centrifuged at 14,000×g for 30 minutes at 4° C. The obtained supernatants were used as the samples of a nuclear extract and a cytoplasmic fraction, respectively. These samples were subdivided into appropriate aliquots and stored at −80° C. until the use of them.

In usual preparation, about 20 ml each of the nuclear extract and the cytoplasmic fraction at the protein concentration of 5 mg/ml and 10 mg/ml, respectively, were obtained in the scale of this working example.

EXAMPLE 5

(Fractionation of a Nuclear Fraction and Cytoplasmic Fraction Using Phosphocellulose)

Cationic-ion exchange phosphocellulose (P11: Whatman) was employed for the fractionation of a cell extract. Procedures for the fractionation were always conducted at 4° C. Distilled water was added to 10 g of dried phosphocellulose to be 500 ml of a phosphocellulose suspension. The suspension was well stirred and allowed to stand still for 30 minutes. To remove phosphocellulose with smaller particle sizes the supernatant of the suspension was removed and distilled water of the same volume as the removed supernatant was added to the remaining phosphocellulose.

These procedures were repeated several times in order to obtain the Phosphocellulose with a uniform particle size. Next, in order to activate the Phosphocellulose, each one gram of the phosphocellulose with a uniform particle size on the basis of the dried weight was suspended in 50 ml of 0.5 N HCl solution and the suspension was allowed to stand for 5 minutes. The phosphocellulose was collected on two sheets of filter paper (Whatman: 3 MM Chr) placed in Buchner funnel and washed with an excess amount of distilled water until the pH value recovered to a neutral range. The pH value of the filtrate was measured using BTB pH test paper to confirm the pH value. The phosphocellulose on the filter paper was transferred into a beaker and resuspended in 0.5 N NaOH solution. The suspension was allowed to stand for 5 minutes. The phosphocellulose was washed in the same manner as described above. Finally, the phosphocellulose was suspended in 0.5 N HCl solution once more and washed again. As a result, activated phosphocellulose was obtained.

The activated phosphocellulose was filled into a column (BIORAD: 731-1550), so that the column volume became 10 ml. The filled column was washed with 100 ml of Buffer D (20 mM HEPES (pH 7.9), 20% (v/v) glycerol, 1 M KCl, 1.2 mM EDTA, 0.5 mM PMSF, 1 mM DTT) containing 1 N KCl and then equilibrated with 100 ml of Buffer D containing 0.1 M KCl. Each 5 ml of a nuclear extract and a cytoplasmic fraction from Jarkat cells was applied on the column. The applied column was eluted stepwise with Buffer D at various salt concentrations of KCl, that is, the elution was conducted stepwise with Buffer containing 0.1 M KCl, 0.32 M KCl, 0.35 M KCl or 1 M KCl. Each eluted fraction was dialyzed against Buffer D, subdivided into appropriate aliquots and stored at −80° C. until the use of them.

The flow rate was adjusted to be 8 ml/minute. To confirm the completion of each step of protein-elution with each salt concentration buffer, absorbance at the wave-length of 280 nm was measured with UV detector (GILSON: MODEL 111B) during the fractionation.

First, 5 ml of a cytoplasmic fraction (protein concentration: 12 mg/ml) was applied on the above column. As a result, 30 ml of 0.1 M fraction (P.1; protein concentration: 1.12 mg/ml), 39 ml of 0.3 M fraction (P.3; protein concentration: 0.23 mg/ml), 37 ml of 0.5 M fraction (P.5; protein concentration: 0.07 mg/ml), and 53 ml of 1.0 M fraction (P1.0; protein concentration: 0.02 mg/ml) were obtained.

Next, a nuclear extract fraction was also fractionated using the phosphocellulose column in the same manner.

EXAMPLE 6
(Isolation of Proteins Using Microspheres)

A process of isolation and purification of E3330-binding proteins using E3330-immobilized particles is illustrated in the FIG. 2 and described as follows.

(a) Microspheres and a fraction obtained through the fractionation using a phosphocellulose column in working Example 5 above were mixed and centrifuged to separate substances binding to E3330 which was immobilized on particles from the mixture. The centrifugation procedure for separation was conducted at 15,000×g for 5 minutes at 4° C. All procedures in the above were conducted at 4° C.

(b) First, 1 mg each of E3330-not-immobilized SG-EGDE particles and E3330-immobilized SG-EGDE particles were washed three times with 400 μl of Buffer D' (20 mM HEPES (pH 7.9), 10% (v/v) glycerol, 0.1 M KCl, 0.2 mM EDTA, 1 mM DTT) in which glycerol concentration was 10% instead of 20% in Buffer D. The E3330-not-immobilized SG-EGDE particles were dispersed in 1 ml of 1 M Tris-HCl buffer solution (pH 7.4) and allowed to stand still at 4° C. for at least 24 hours in order to mask epoxy groups of EGDE. These particles were used as a reference control against E3330-immobilized SG-EGDE particles. To these washed E3330-not-immobilized SG-EGDE particles and E3330-immobilized SG-EGDE particles, 200 μl each of P.1, P.3, P.5 or P1.0, which were obtained through the fractionation of a cytoplasmic fraction using a phosphocellulose column, was added and mixed. These mixtures were allowed to stand still for 30 minutes with intermittently stirring at intervals of 10 minutes in order to bind proteins possessing E3330-binding abilities to E3330 which was immobilized on the particles. The mixture was centrifuged and the supernatant was discarded. The pellet was washed three times with 500 μl of Buffer D' to remove non-specific binding substances as much as possible.

Subsequently, the washed pellet was eluted three times with Buffer D' containing 50 μl of 1 M KCl, so that the proteins possessing E3330-binding abilities were dissociated and eluted from E3330 immobilized on the particles. The wash solution and eluate solution were stored at −80° C.

(c) The detection of the proteins possessing E3330-binding abilities was conducted by electrophoresis on a 10% SDS-polyacrylamide gel (SDS-PAGE) using 25 μl each of the first, second or third eluate solution obtained from the E3330-immobilized SG-EGDE particles and E3330-not-immobilized SG-EGDE particles used as a reference control. The proteins possessing E3330-binding abilities were collected with more than 70% yield in the first elution and further collected with more than 90% yield in the first and second elutions. In this experiment, 4×SDS sample dye (200 mM Tris-HCl (pH 6.8), 500 mM β-mercaptoethanol (μ-ME), 8% SDS, 0.4% BPB) was used instead of 4×SDS sample dye in order to prevent the electrophoresis from being disordered due to such high concentration of the salts. The electrophoresed gel was subjected to silver staining and the proteins specifically binding to E3330 were identified in comparison with the results of the reference control. As a result, in the P.5 fraction a protein band with a molecular weight of about 38 kDa which was not observed in the reference control was clearly observed, suggesting that the protein was specifically binding to E3330. Concerning the other fractions, there were no significant differences in the protein bands of the eluate solution with 1 M KCl, compared with the results of the reference control.

The above procedure was repeated and finally 5 μg of E3330-binding protein was obtained.

EXAMPLE 7
(Evaluation of Specific-binding Abilities Against E3330)

Two kinds of experiments were conducted to confirm that the protein with a molecular weight of about 38 kDa in the P.5 fractions from cytoplasmic fractions and nuclear extracts of Jurkat cells was specifically bound to E3330.

The first one was a competitive binding-inhibitory experiment. When in the step of a procedure for the addition of P.5 fraction of the cytoplasmic fraction fractionated using the phosphocellulose (200) to SG-EGDE particles free E3330 at the same moles of the $NH_2$-E3330 immobilized on the particles or free $NH_2$-E3330 at ten times more moles than the immobilized $NH_2$-E3330 were added simultaneously, the protein possessing specifically binding abilities to E3330 immobilized on the particles would be bound to free E3330 or free $NH_2$-E3330, resulting in a lower yield in the isolation using the particles. As E3330 was insoluble in water, E3330 was dissolved in EtOH, diluted with Buffer D and then added to the particles (the final concentration of EtOH was 2%). As a result, it was confirmed that the yield of the protein with a molecular weight of about 38 kDa was lowered, indicating that the protein was specifically bound to E3330.

EXAMPLE 8

Next, the other experiment was conducted by varying the amount of NH$_2$-E3330 immobilized on the SG-EGDE particles. In the present study the maximum amount of the immobilized E3330 derivatives is 0.4 μmol per 1 mg of SG-EGDE particles. Under these conditions, about 5 to 6 molecules of E3330 derivatives are immobilized on the 1 mm$^2$ of the surface of the particles. This experimental study was conducted in case where the amount of the immobilized E3330 derivatives was 0.2 μmol or 0.4 μmol per 1 mg of SG-EGDE particles. However, in the present invention, amounts of compounds immobilized on the particles are varied depending on the properties of the immobilized compounds, conditions of immobilization and so on. The amounts are not defined and are generally varied between a few molecules and hundred molecules. As a result, it was confirmed that the yield of the protein with a molecular weight of about 38 kDa increased as the immobilized amount increased. The identification of the specific protein was conducted by electrophoresis using SDS-PAGE.

EXAMPLE 9
(Determination of Amino Acid Sequence of E3330-binding Protein)

The obtained E3330-binding protein was dialyzed two times against one liter of Buffer D for 2.5 hours at 4° C. in order to remove the contaminated KCl that was used as an eluent solution of such as high concentration of 1.0 M of KCl. In order to concentrate the sample, after the dialysis was completed, the dialyzed sample was transferred into an ultra-centrifugation tube (BECKMAN: No. 331372) to which trichloroacetic acid (TCA: MERCK) and deoxycholic acid (DOC: Sigma) were added so that the final concentrations would be 10% and 0.8 mg/ml, respectively. The mixture was stirred well and allowed to stand still for 30 minutes on ice. Then, the mixed sample was ultra-centrifuged at 28 krpm, for 15 minutes at 4° C. (BECKMAN: Rotor SW 41 Ti). The obtained precipitation was dissolved in 10 ml of acetone. After standing still for 10 minutes at room temperature, the solution was ultra-centrifuged again. The obtained precipitation was allowed to stand still for 10 minutes on ice to be dried. Thus, the sample was concentrated.

Finally, the concentrated sample was dissolved in 50 μl of 1×SDS sample dye and transferred into a sample tube (Eppendorf: No. 0030 102.002). In this procedure, the remaining sample in the ultracentrifugation tube was rinsed with additional 10 μl of 1×SDS sample dye and pooled in order to collect the remaining sample.

As TCA and DOC were remaining in the sample, 3 μl of 1 M Tris-HCl (pH 7.9) was added for the purpose of neutralization. Then, the sample was stored at −80° C.

To analyze the amino acid sequence of E3330-binding protein, the protein was subjected to peptide-fragmentation. First, the sample was electrophoresed with pre-stained SDS-PAGE standard (BIO-RAD) on a 10% SDS-polyacrylamide gel and the protein was transferred into PVDF membrane (MILLIPORE: immobilon transfer membrane) from the polyacrylamide gel using Mini trans blott module kit (BIO-RAD). Prior to the blotting, the PVDF membrane was soaked in methanol for 15 seconds and subsequently it was soaked in a blotting buffer solution (10 mM CAPS-NaOH (pH 11), 10% methanol) for more than 5 minutes. The blotting apparatus was placed on the anode side down and two sheets of fiber pad, two sheets of 3 MM paper, PVDF membrane, the gel, two sheets of 3 MM paper and two sheets of fiber pad were laid in the blotting apparatus in that order, avoiding bubbles. The apparatus was placed in an electrophoretic bath filled with a blotting buffer solution. The bath was being chilled with ice and 0.3 A of electric current was turned on for minutes to blot the protein into PVDF membrane.

In case where the proteins blotted on the membrane were enzymatically digested, Lysil Endopeptidase (Wako Pure Chemicals) was employed as the digestive enzyme. As a buffer solution for the digestive reaction 20 mM Tris-HCl (pH 8.8) with 8% acetonitrile was used. The amount of the enzyme was one tenth of the protein for the digestion (g/g). First, a half amount of the enzyme was added, followed by stirring with shaking for several seconds. Then, the other half of the enzyme was added to the above, followed by stirring with shaking at 37° C. for about 24 hours under prevention of light-transmittance. After the completion of the reaction, the digested fluid was carefully collected, paying attention to the PVDF membrane not to be sucked up. The remaining PVDF membrane was washed with 100 μl of 8% acetonitrile. The washing fluid was collected in the same manner as the above and pooled. These fluids were centrifuged at 15,000×g for 2 minutes at room temperature in order to completely separate the contaminated PVDF membrane pieces and remove them. In case where the supernatant is directly applied on high performance liquid chromatography (HPLC), highly hydrophilic peptides are eluted in a passing through fraction. Therefore, the supernatant was concentrated by decompression so that the concentration of acetonitrile was reduced. To the concentrated supernatant 0.1% trifluoroacetic acid (TFA) was added so that the volume became 205 μl, which was applied on reversed phase HPLC (ABI: model 130A). C8 column (PERKIN ELMER: 0711-0056) was employed. Flow rate was 50 μl/min and column temperature was 35° C. for development. Elution was conducted as follows; mobile phase was 0.1% TFA and concentration gradient of acetonitrile in the mobile phase was 0% for the first 5 minutes, 0 to 35% for the next 30 minutes and 35 to 70% for the last 20 minutes. Monitoring protein was conducted using ultraviolet absorption at the wave-length of 215 nm. Each eluted peptide fraction was collected at each time and stored at −80° C.

Gas phase protein sequencer (ABI: model 477A protein sequencer) was used for amino acid sequence analysis on the peptides. Polybrene (ABI) was used as the carrier. As a result, three amino acid sequences of peptides were determined. The obtained sequences were GLDWVK (SEQ ID NO: 1)/AAGEGPALYEDPPD (SEQ ID NO: 2)/GAVAEDGDEL (SEQ ID NO: 3). These amino acid sequences were analyzed using a computer and determined to be completely identical with the amino acid sequences of N-terminal flanking region of redox protein, Ref-1 which participates in oxidation-reduction reaction. The Ref-1 has been reported to possess 318 amino acid residues with a molecular weight of 38 kDa. The protein obtained through the isolation and purification in this working example possesses the same molecular weight. Therefore, E3330-binding protein is probably identical with Ref-1. Amino acid sequence of Ref-1 is as follows (SEQ ID NO:4 length of sequence 318 amino acids):

```
M P K R G K K G A V A E D G D E L R T E P E A K K S K T A A
1                   10                  20                  30

K K N D K E A A G E G P A L Y E D P P D Q K T S P S G K P A
31                  40                  50                  60

T L K I C S W N V D G L R A W I K K K G L D W V K E E A P D
61                  70                  80                  90

I L C L Q E T K C S E N K L P A E L Q E L P G L S H Q Y W S
91                  100                 110                 120

A P S D K E G Y S G V G L L S R Q C P L K V S Y G I G D E E
121                 130                 140                 150

H D Q E G R V I V A E F D S F V L V T A Y V P N A G R G L V
151                 160                 170                 180

R L E Y R Q R W D E A F R K Y L K G L A S R K P L V L C G D
181                 190                 200                 210

L N V A H E E I D L R N P K G N K K N A G F T P Q E R Q G F
211                 220                 230                 240

G E L L Q A V P L A D S F R H L Y P N T P Y A Y T F W T Y M
241                 250                 260                 270

M N A R S K N V G W R L D Y F L L S H S L L P A L C D S K I
271                 280                 290                 300

R S K A L G S D H C P I T L Y L A L
301                 310         313
```

EXAMPLE 10
(Production of E3330-binding Protein by Gene Recombination)

(a) The procedures for preparation of cDNA clones of E3330-binding protein and analysis on the binding activity of the protein produced through gene expression of recombinant cDNA clones in *Eschenchia coli* (*E.coli*) against E3330 were conducted as follows.

On the basis of the determined amino acid sequences E3330-binding factor is considered most probably to be Ref-1. Therefore, cDNA clones of Ref-1 were prepared and the recombinant cDNA clones were expressed in *E.coli* to obtain recombinant proteins. Then, the binding activity of the protein against E3330 was investigated.

(b) First, RNA was prepared. When RNA was prepared, ultra-centrifugation tubes (BECKMAN: 331372), bucket (BECKMAN: for SW 41Ti) and bucket cap (BECKMAN: for SW 41Ti) were preliminarily soaked in 2% absolve solution (DUPONT; 20 ml of absolve was diluted with distilled water to be 1000 ml) on the day before the preparation to remove contaminated RNase activities as much as possible. They were thoroughly rinsed with distilled water just before the use. Cultivation medium of Jurkat cells cultured up to 4.2 liter ($7.6 \times 10^9$ cells) was transferred to 500-ml-centrifugation tubes and centrifuged at 500×g for 5 minutes at 4° C. to collect the cells. The collected cells were washed two times with PBS(−). The centrifugation conditions for washing were 700×g for 5 minutes at 4° C. using 50-ml-centrifugation tubes. At that time packed cell volume (PCV) was simultaneously measured.

These cells were thoroughly suspended in 10-fold PCV of guanidium solution (4 M guanidium thiocyanate, 0.1 M Tris-HCl pH 7.5, 1% (v/v) β-ME). The suspension was passed through an injection needle of 18 G (1.2 mm) (TERUMO: NN-1838R) twenty times and further through an injection needle of 25 G (0.5 mm) (TERUMO: SS-20ES) to cut DNA strands into fragments. To the resultant suspension 10% N-lauroylsarcosine was added and thoroughly stirred, so that the final concentration of lauroylsarcosine became 0.5%. Then, 3 ml of each aliquot of the mixture was carefully placed over the phase of 9 ml of CsCl/EDTA solution (5.7 M CsCl, 0.01 M EDTA pH 7.5) which was preliminarily poured into an ultra-centrifugation tube. The ultracentrifugation tubes were placed in the bucket and bucket cap was fastened. Then, the bucket was fixed in a rotor (SW 41Ti) and ultracentrifuged at 32 kprm for 24 hours at 20° C.

The supernatant was carefully discarded thoroughly and the upper part of the ultra-centrifugation tube was cut of f by a cutter. The obtained precipitation was washed with 70% ethanol. Then, the pellet was rinsed three times with 150 μl of TE/SDS solution (10 mM Tris-HCl pH 7.6, 1 mM EDTA, 0.1% SDS) to dissolve the precipitation in TE/SDS solution. The solution was extracted two times with phenol/chloroform, followed by addition of 900 μl of ethanol and 30 μl of 3 M sodium acetate (pH 5.2). The mixture was stored at −80° C. until use. When the concentration was measured, an aliquot of the above stock solution was taken out and centrifuged (15,000×g for 5 minutes at 4° C.). After washing with 70% ethanol (15,000×g for 5 minutes at 4° C.), the precipitation was dissolved in water that was pretreated with diethyl pyrocarbonate (DEPC) (DEPC was added to distilled water so that the final concentration of DEPC became 0.1%, followed by stirring, standing still for about 24 hours and autoclaving. The pretreated water was stored at room temperature.). Absorbance of the solution was determined at the wave-length of 260 nm using DU-64 Spectrophotometer and the amount of RNA was estimated.

(c) Next, complementary single-stranded cDNA was prepared by reverse transcription. An aliquot of RNA (10 μg) obtained in the above procedure was taken out and centrifuged (15,000×g for 5 minutes at 4° C.). The obtained precipitation was washed with 70% ethanol (15,000×g for 5 minutes at 4° C.) and dissolved in 9.8 μl of DEPC-treated water. To the solution 160 ng of 0.5 μg/μl Oligo(dT)$^{15}$ primer (Promega: 5'-TTTTTTTTTTTTTTT-3') was added and heated at 70° C. for 5 minutes. After the heating for 5 minutes, the sample was promptly placed on ice and Preliminarily ice-chilled 28 μl of reaction buffer (a mixture of Reverse Transcriptase attachments, that is, 8 μl of 5×RT Buffer, 4 μl of 0.1 M DTT, 2 μl of 10 mM dNTPs, and 13 μl of distilled water), 1 μl of Ribonuclease inhibitor (TaKaRa: Ribonuclease inhibitor) and 2 μl of Reverse transcriptase (GIBCO BRL: Super ScriptTM RNase H-Reverse Transcriptase) were added to the sample in this order. Then, the mixed sample was promptly subjected to one-hour reaction at 37 C. to elongate the complementary single-stranded cDNA by reverse transcription. At the end of the reaction, the sample was heated at 95° C. for 5 minutes to stop the reaction by heat block. The obtained complementary single-stranded cDNA was stored at −30° C. until use.

(d) Subsequently, oligonucleotides were synthesized for the purpose of amplification of Ref-1 translational region by Long-PCR method. Each base sequence of the synthesized oligonucleotides is shown in the following. Each oligonucleotide possesses individual digestive region by the restriction enzyme from which each oligonucleotides takes its name.

5' Ref-1 XhoI primer:
5'-GTCTCTCGAGATGCCGAAGCGTGGGAAAAAG-3' (SEQ ID NO: 5)

3' Ref-1 BamHI primer:
5'-ATGCGGATCCTTACAGTGCTAGGTATAGGGT-3' (SEQ ID NO: 6)

The synthesized oligonucleotides were heated at 55° C. for 8 hours to be deprotected. The deprotected oligonucleotides were subdivided into aliquots, dried under vacuum and dissolved in diluted (1 in 10) buffer of TE (10 mM Tris-HCl pH 7.9, 1 mM EDTE). PCR was conducted with the above two kinds of oligonucleotides, employing the prepared single-stranded cDNA as templates. PCR kit (XL PCR kit: PERKIN ELMER) was employed for the PCR procedures. There are two kinds of reaction solutions (Lower Layer and Upper Layer). The Lower Layer contains 40 pmol each of 5'-terminal primer and 3'-terminal primer, dNTPs of final concentration of 0.8 mM, Mg(OAc)2 of final concentration of 1.4 mM and 12 μl of 3.3×XL Buffer II. The final volume was made to be 40 μl. On the other hand, the Upper Layer contains 1 μl of the single-stranded cDNA templates, rTth DNA Polymerase, XL 4U and 18 μl of 3.3×XL Buffer II. The final volume was made to be 60 μl.

First, GEM 100 WAX (PERKN ELMER) was placed on the Lower Layer of a sample tube and heated at 80° C. for 5 minutes using a gene amplification apparatus, followed by cooling at 25° C. for one minute, so that the WAX was solidified on the Lower Layer. Thereon Upper Layer was placed and subjected to the reaction using a gene amplification apparatus according to the following scheme; at 94° C. for one minute, 16 cycles of (at 94° C. for 15 seconds, at 60° C. for 10 minutes), 12 cycles of (at 94° C. for 15 seconds, at 600° C. for 10 minutes (elongated by 15 seconds in every cycle)), and at 72° C. for 10 minutes. After the completion of the reaction, the WAX which was solidified on the Upper Layer was holed through and the reaction solution was transferred, followed by chloroform extraction and ethanol precipitation. The amplified DNA fragments were digested by XhoI and BamHI (TOYOBO) and directly subjected to agarose gel electrophoresis. A part of the agarose gel containing the DNA fragments was isolated, followed by phenol/chloroform extraction and ethanol precipitation to purify the DNA fragments.

(e) As the E.coli expression vector, pET14b (Novagen) was employed. The DNA fragments purified in the above procedure were ligated with the isolated and purified pET14b XhoI/BamHI-digested fragments in order to construct the E.coli expression plasmids (pET/Ref) which would express the recombinant protein of Ref-1 wild type.

The E.coli possessing pET14b-derived E.coli expression plasmids expresses His-Tag fused recombinant protein of which N-terminal region is a peptide consisting of six histidines.

EXAMPLE 11

(Confirmation of the Binding Ability of Ref-1 Against E3330)

(a) The binding ability of the recombinant protein obtained in the above procedure against E3330 was investigated using E3330-immobilized particles. As a result, it was certainly confirmed that the recombinant protein of Ref-1 specifically bound to E3330. Furthermore, it was confirmed that E3330 bound to Ref-1 in Far Western method using $^{14}$C-labeled E3330. Therefore, Ref-1 is regarded as intracellular receptor to E3330.

(b) Ref-1 consists of a domain possessing redox activity in its N-terminal region and consists of another domain possessing AP nuclease activity, that severs apurinic/apyrimidinic single-stranded DNA and inserts nick, in its C-terminal region. Therefore, it was investigated whether E3330 would inhibit these activities or not in the next experiment.

Figure 3A:
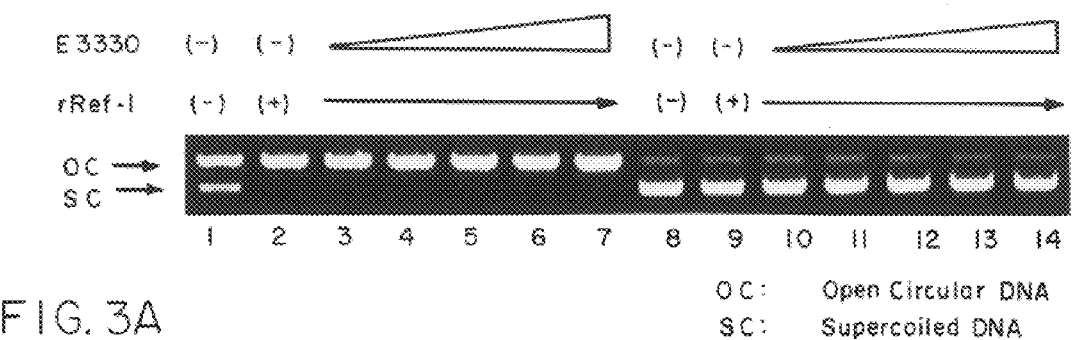
FIG. 3(A) shows the effects of E3330 on AP endonuclease activity of Ref-1.
Figure 3B:
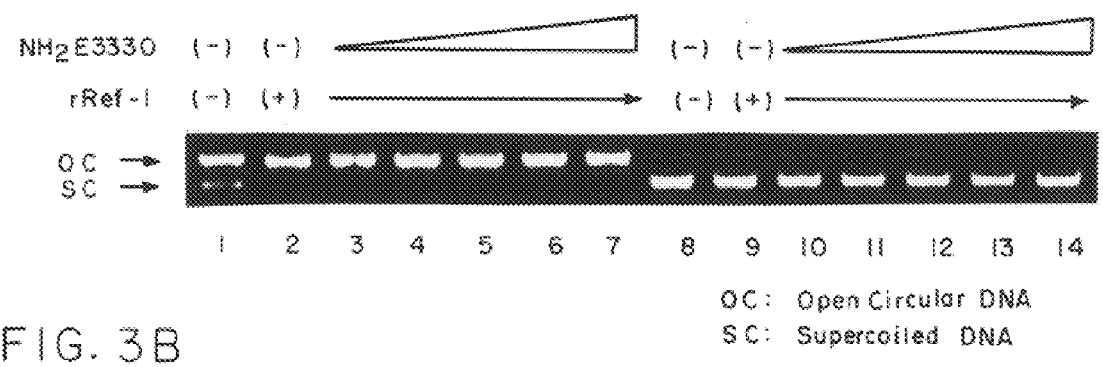
FIG. 3(B) shows the effects of $NH_2$-E3330 on AP endonuclease activity of Ref-1.

First, concerning AP nuclease activity, the plasmid pBluescript SK+DNA (50 μg) was treated with 50 mM sodium citrate (pH 3.5) at 60° C. for 15 minutes, followed by dialysis in 50 mM Tris-HCl (pH 7.4) at 4° C. for about 24 hours. This AP plasmid DNA possesses supercoiled circular DNA structure. This DNA was suspended in nuclease buffer solution (10 mM Tris-HCl (pH 8.0), 5 mM $MgCl_2$, 1 mM EDTA, 0.01% NP-40), to which the recombinant Ref-1 was added, resulting in insertion of nick and open circular DNA structure. However, as shown in FIG. 3, the AP nuclease activity of the Ref-1 was not inhibited by E3330.

(c) Next, effects of Ref-1 on a redox activity were investigated.

Figure 4A:
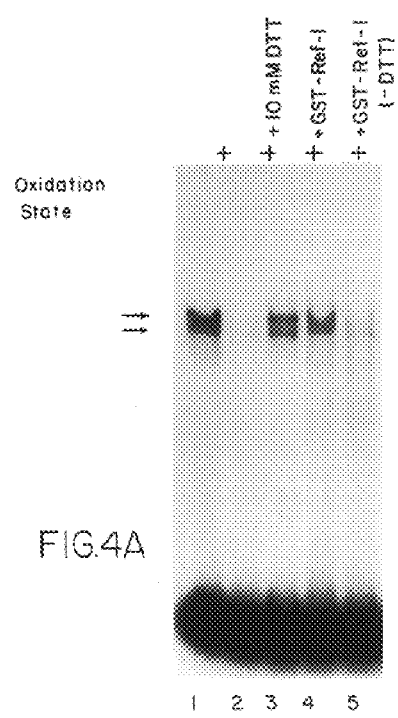
FIGS. 4(A) and 4(B) show the enhancement of the DNA-binding activity of NF-$_\kappa$B by recombinant rRef-1 and the repression of the recombinant rRef-1 activity by E3330.
Figure 4B:
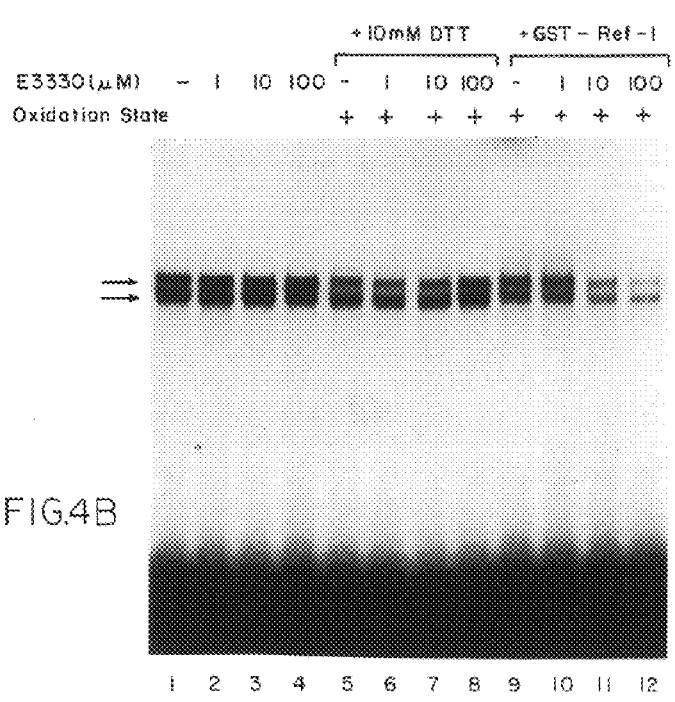

The obtained results are shown in FIG. 4. Prior to the conduction of the investigation, there are some considerations. Transcription factor NF-$_\kappa$B possesses plural cystine residues in its amino acid sequence. There are two cases; one is an oxidized condition where these cystine residues are bound to each other through an S—S bond; and the other one is a reduced condition where they are individually existing with an SH-group. Therefore, NF-$_\kappa$B was treated with dithiothreitol (DTT) that is known as a reductant to make the state of NF-$_\kappa$B to be reduction. As a result, DNA-binding ability of the reduced NF-$_\kappa$B was increased, that was confirmed by a gel-shift assay. Ref-1 possessing a redox activity was added to NF-$_\kappa$B which was partially purified from Jurkat cells, resulting in increase in DNA-binding ability, that was confirmed by a gel-shift assay. Furthermore, the enhancement of the DNA-binding activity of NF-$_\kappa$B by Ref-1 was reduced by the addition of E3330 to the reaction mixture. However, E3330 did not inhibit the increase in the DNA-binding activity of NF-$_\kappa$B by DTT. Therefore, it was revealed that E3330 specifically inhibits the DNA-binding activity of NF-$_\kappa$B.

Figure 5:
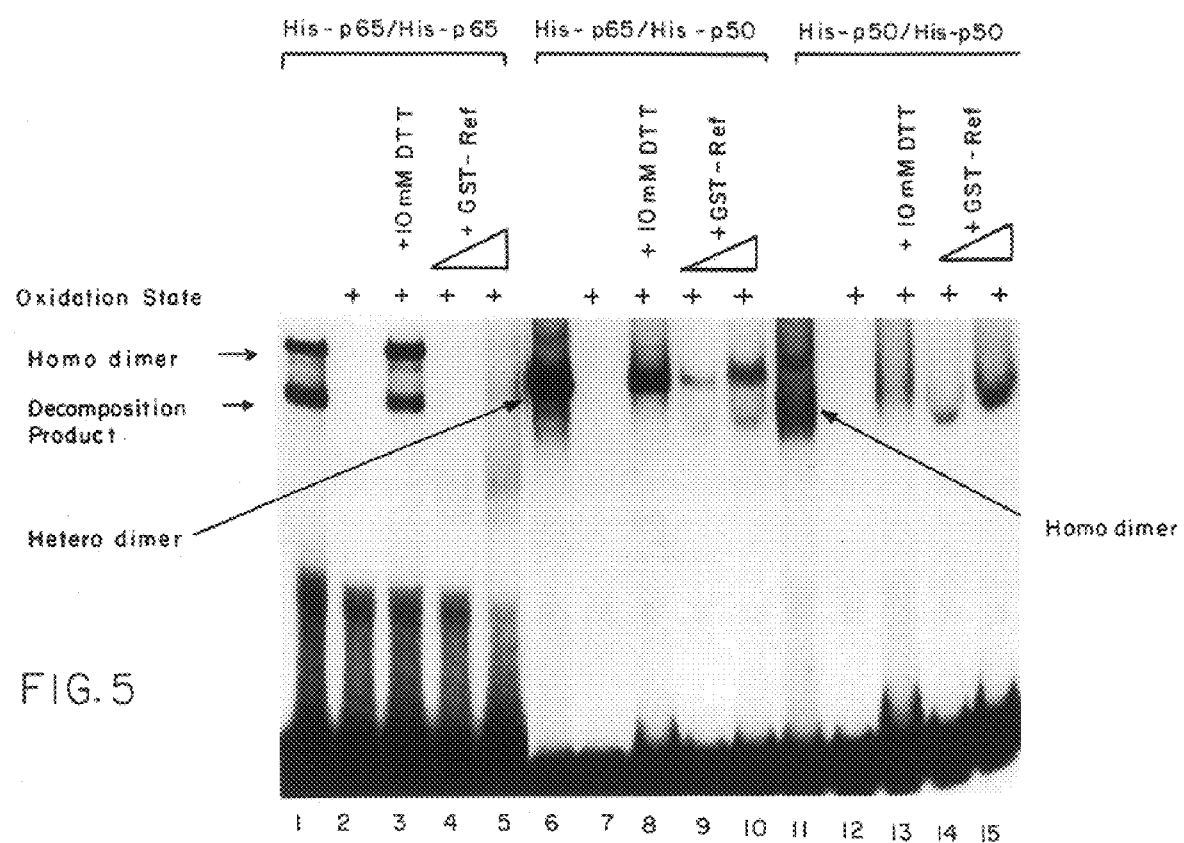
FIG. 5 shows the effects of recombinant rRef-1 on the DNA-binding activities of r-p65 and/or r-p50.

(d) NF-$_\kappa$B is a hetero-dimer consisting of two subunits (p65 and p50). The molecular weights of those two subunits p65 and p50 are 65 kDa and 50 kDa, respectively. The His-tag recombinant proteins of those p65 and p50 subunits were prepared using baculovirus expression system. Then, it was investigated by gel-shift assay whether E3330 had effects on p65 or on p50. The obtained results are shown in FIG. 5. DNA-binding ability of p65/p65 homo-dimer under reduced conditions by the addition of DTT was significantly enhanced, but the enhancement was not observed by the addition of Ref-1. On the other hand, DNA-binding ability of p50/p50 homo-dimer and p65/p50 hetero-dimer was enhanced by the addition of either DTT or recombinant Ref-1. Therefore, it was revealed that Ref-1 had effects on p50, one of the subunits NF-$_\kappa$B. The enhancement of DNA-binding ability of p50/p50 homo-dimer or p65/p50 hetero-dimer by the addition of Ref-1 was reduced by the addition of E3330. As NF-$_\kappa$B recognizes a specific base sequence and binds to the specific DNA sequence, binding to DNA is the minimum requirement for NF-$_\kappa$B to function as a transcriptional factor. This binding step is regulated by Ref-1, indicating that Ref-1 is at least an intracellular factor activating transcription factor, NF-$_\kappa$B with respect to DNA-binding step. Moreover, it was revealed that E3330 inhibits the activation induced by Ref-1.

Figure 6:
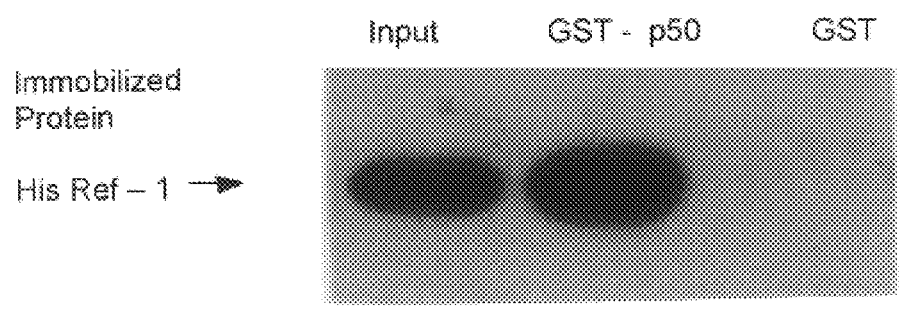
FIG. 6 shows the procedure and the results of the GST pull-down assay.

(e) In addition, GST pull down assay was conducted to confirm that Ref-1 specifically bound to p50 subunit of NF-$_\kappa$B. The obtained results show that Ref-1 really binds to p50 of GST-tag (GST-p50), as indicated in FIG. 6.

EXAMPLE 12
(Preparation of Mutational Recombinant Proteins of Ref-1)

Figure 7:
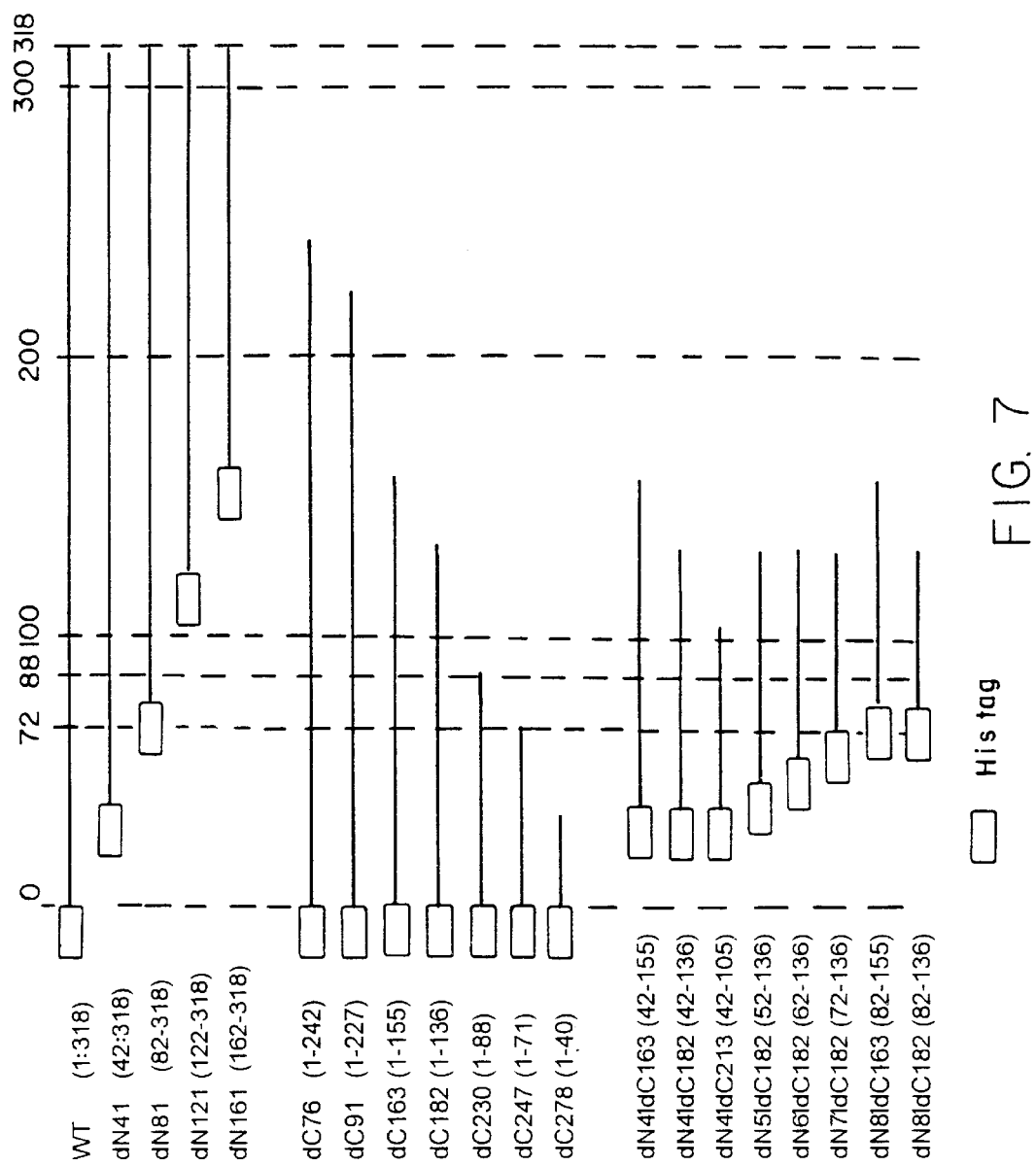
FIG. 7 is a schematic for the structure of each recombinant protein of Ref-1 expressed by various deletion mutants.

(a) In order to confirm that Ref-1 bound to E3330, a series of different quantities of N-terminal and C-terminal flanking regions of Ref-1 deletion mutant strains were prepared using pET/Ref, as described in the following. Then, these recombinant proteins were expressed in *E.coli* and purified using a nickel column and a glutathione column to investigate whether they bound to E3330-immobilized particles or not. These mutational recombinant proteins of Ref-1 including a wild type are schematically shown in FIG. 7.

(b) Preparation of pET/RefdC76, pET/RefdC91, pET/RefdC163 and pET/RefdC182

The prepared pET/Ref, 10 μg, was digested with BamHI and AatII (TOYOBO), extracted with phenol/chloroform and precipitated with ethanol. These pET/Ref BamHI/AatII digested fragments were dissolved in 100 μl of the buffer solution which was prepared through dilution (1 in 10) of 10×ExoIII Buffer (500 mM Tris-HCl (pH 8), 50 mM MgCl$_2$, 100 mM β-ME) attached to Exonuclease III (ExoIII: TaKaRa). Subsequently, 180 U of ExoIII was added to the above solution, followed by incubation at 25° C. for 5, 10, 15, 20, 25, 30, 40, 50, or 60 minutes, for the purpose of degradation of the pET/Ref BamHI/AatII digested fragments in the direction of 3 to 5'. Since ExoIII is inhibited by the addition of Zn+, 100 μl of the buffer solution which was prepared through dilution (1 in 10) of 10×Mung Been Buffer (300 mM CH$_3$COONa (pH 4.6), 1 M NaCl, 10 mM (CH$_3$COO)$_2$Zn, 50% Glycerol) attached to Mung Been Nuclease (TaKaRa) was added to each of the reaction mixtures to stop the degradation. The resultant reaction mixtures were incubated at 65° C. for 5 minutes to inactivate the eznyme completely. Subsequently, 50 U of Mung Been Nuclease was added to the above solutions, followed by incubation at 37° C. for 30 minutes, for the purpose of degradation of the portions of single-stranded DNA through the degradation by ExoIII. Then, the resultant solutions were subjected to extraction with phenol/chloroform and precipitation with ethanol. The DNA termini were repaired with Klenow Fragment (terminal smoothing of DNA) to make the DNA termini completely smooth. Then, the resultant solutions were subjected to extraction with phenol/chloroform and precipitation with ethanol, followed by digestion with XhoI. Through the above procedures, translational regions of Ref-1 with various length-deletion in its C-terminal region, with which the N-terminus was the XhoI-digested terminus and the C-terminus was the smooth terminus, were obtained.

Three fragments, that is, one of these various DNA fragments, isolated and purified pET14b XhoI/BamHI-digested fragment and BamHI Linker, were ligated to each other in order to construct plasmids expressing recombinant Ref-1 deletion mutants in *E.coli*. The base sequences of BamHI Linker are shown in the following. Every frame of the Linker was designed to contain termination codon. The preparation method for the Linker is the same as the above method by which various kinds of double-stranded DNA with ligation sequence for each transcriptional factor were prepared in the above.

BamHI Linker

: 5'-TAACTAACTAG-3' (SEQ ID NO: 7)

: 3'-ATTGATTGATCCTAG-5' (SEQ ID NO: 8)

Names for plasmids expressing recombinant Ref-1 deletion mutants in *E.coli* were taken from the number of deleted amino acid residues from their C-termini after the translation. The names are described in the following in order of the number: pET/RefdC76 (76 amino acid residues from the C-terminus were deleted), pET/RefdC91 (91 amino acid residues from the C-terminus were deleted), pET/RefdC163 (163 amino acid residues from the C-terminus were deleted) and pET/RefdC182 (182 amino acid residues from the C-terminus were deleted).

(c) Preparation of pET/RefdC230, pET/RefdC247 and pET/RefdC278

Through the same method as described in the above, pET/RefdC230 (230 amino acid residues from the C-terminus were deleted), pET/RefdC247 (247 amino acid residues from the C-terminus were deleted) and pET/RefdC278 (278 amino acid residues from the C-terminus were deleted) were constructed.

(d) Preparation of pET/RefdN41, pET/RefdN81, pET/RefdN121 and pET/RefdN161

A series of these recombinant Ref-1 N-terminal deletion mutants expressing in *E.coli* were amplified by Long-PCR method using synthesized oligonucleotides. Each base sequence of the synthesized oligonucleotides is shown in the following. Each oligonucleotide possesses individual digestive region by the restriction enzyme from which each oligonucleotide takes its name.

5' RefdN41 XhoI primer:

5'-ATGCCTCGAGATGCCAGCCCTGTATGAGGACC-3' (SEQ ID NO: 9)

5' RefdN81 XhoI primer:

5'-ATGCCTCGAGATGGATTGGGTAAAGGAAGAA-GCC-3' (SEQ ID NO: 10)

5' RefdN121 XhoI primer:

5'-ATGCCTCGAGATGCCTTCGGACAAGGAAGGG-T-3' (SEQ ID NO: 11)

5' RefdN161 XhoI primer:

5'-ATGCCTCGAGATGTTTGACTCGTTTGTGCTGG-TA-3'(SEQ ID NO: 12)

The synthesized oligonucleotides were heated at 55° C. for 8 hours to be deprotected. The deprotected oligonucleotides were subdivided into aliquots, dried under vacuum and dissolved in diluted (1 in 10) buffer of TE (10 mM Tris-HCl (pH 7.9), 1 mM EDTA).

One of the above four kinds of oligonucleotides and 3'Ref-1 BamHI primer were combined and subsequent procedures were the same as previously described to conduct PCR. The amplified DNA fragments were individually digested by Xhoi and BamHI (TOYOBO) and directly subjected to agarose gel electrophoresis. A part of the agarose gel containing the DNA fragments was isolated, followed by phenol/chloroform extraction and ethanol precipitation to purify the DNA fragments. One of these various DNA fragments, isolated and purified pET14b XhoI/BaHI-digested fragment and BamHI Linker, were ligated to each other in order tb construct pET/RefdN41 (41 amino acid residues from the N-terminus were deleted), pET/RefdN81 (81 amino acid residues from the N-terminus were deleted), pET/RefdN121 (121 amino acid residues from the N-terminus were deleted) and pET/RefdN161 (161 amino acid residues from the N-terminus were deleted), respectively.

(e) Preparation of pET/RefdN41dC163, pET/RefdN41dC182 and pET/RefdN41dC213

First, pET/RefdN41 was digested with PvuII and XhoI, and subjected to agarose gel electrophoresis. A part of the agarose gel containing only translational region was isolated. On the other hand, pET/RefdC163, pET/RefdC182 and pET/RefdC213 were digested with PvuII and BamHI, and subjected to agarose gel electrophoresis. Each part of the agarose gel containing only translational region was individually isolated and prepared. The same procedures, as described in the above, were conducted to ligate to each other in order to construct pET/RefdN41dC163 (41 amino acid residues from the N-terminus were deleted and 163 amino acid residues from the C-terminus were deleted), pET/RefdN841dC182 (41 amino acid residues from the N-terminus were deleted and 182 amino acid residues from the C-terminus were deleted) and pET/RefdN41dC213 (41 amino acid residues from the N-terminus were deleted and 213 amino acid residues from the C-terminus were deleted), respectively.

(f) Preparation of pET/RefdN51dC 182, pET/RefdN61dC182, pET/RefdN71dC182, pET/RefdN81dC163 and pET/RefdN81dC182

The same procedures, as described in the above, were conducted to construct each deletion mutant.

EXAMPLE 13

(Binding Assay of Mutational Recombinant Proteins of Ref-1 Expressed in *E.coli* Against E3330)

Figure 8:
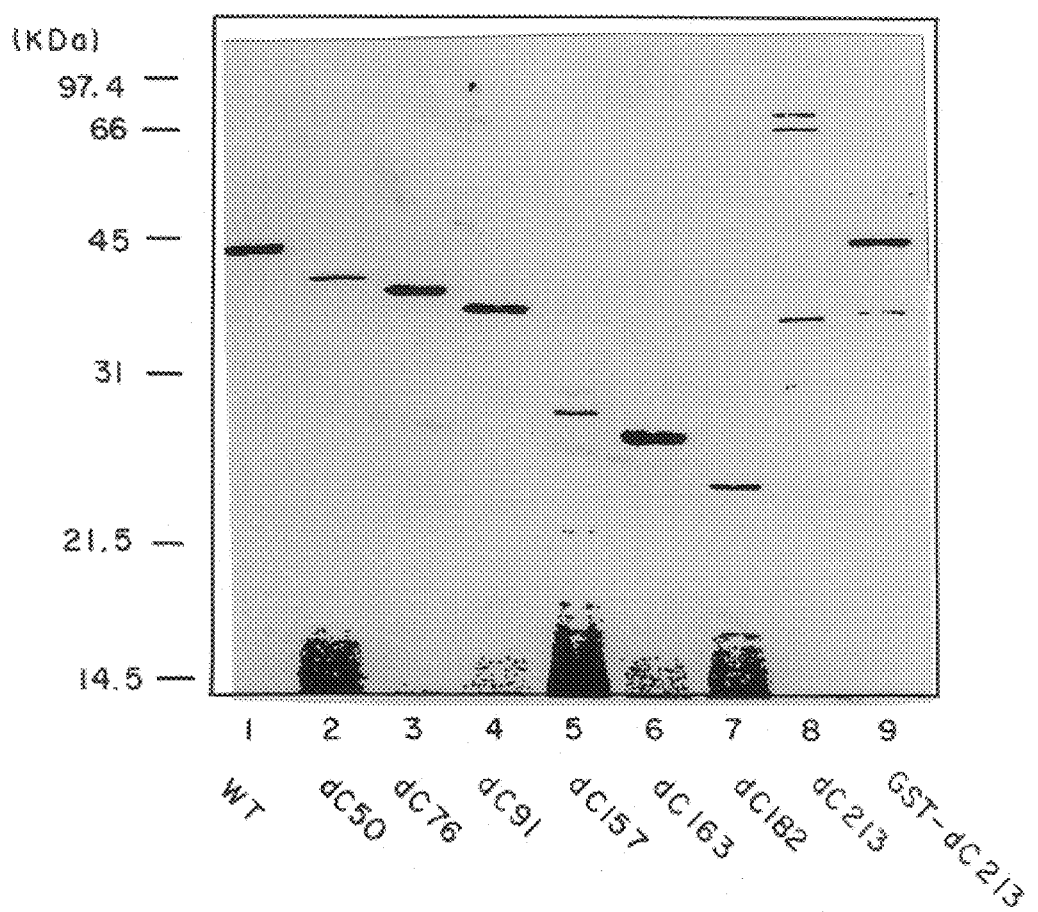
FIG. 8 shows the results of binding assays against E3330 using the recombinant proteins of Ref-1 expressed in *E.coli* by various deletion mutants.
Figure 9:
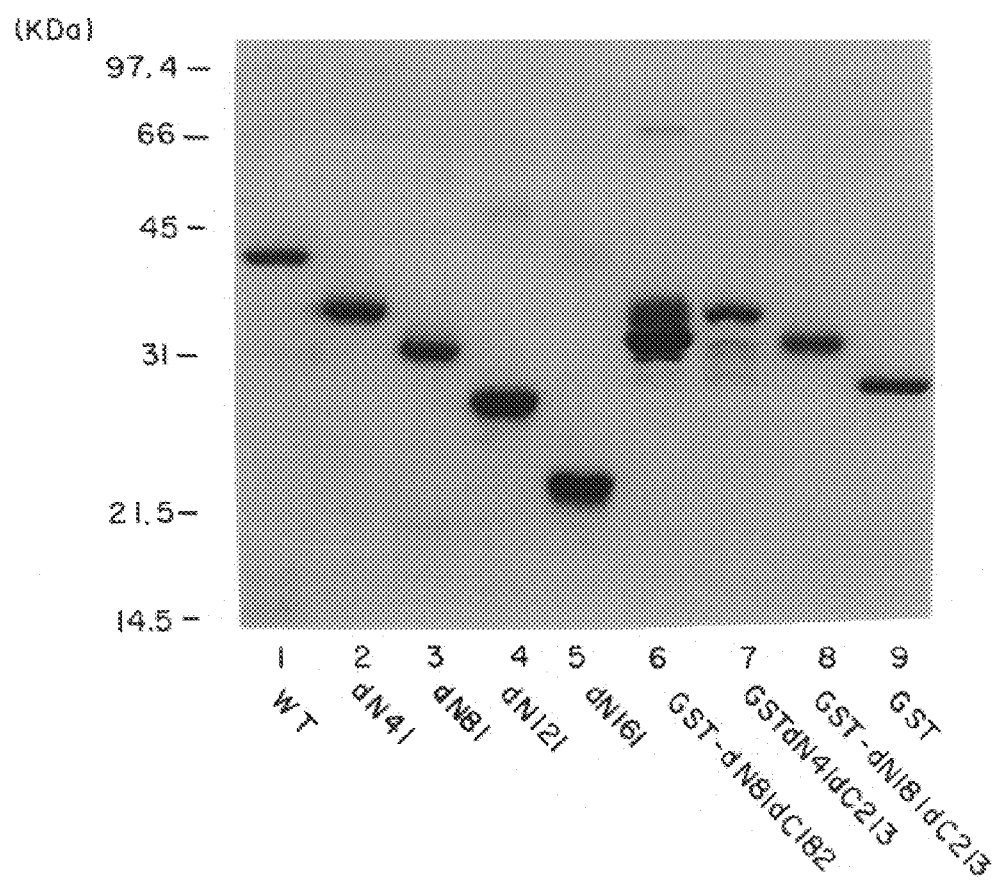
FIG. 9 shows the results of binding assays against E3330 using the recombinant proteins of Ref-1 expressed in *E.coli* by various deletion mutants.

First, wild-type recombinant proteins of Ref-1 and mutational recombinant proteins of Ref-i were expressed in *E.coli* and purified using His Bind Resin or Glutathione Sepharose 4B. Then, each purified protein was subjected to SDS-PAGE and stained using Rapid Stain CBB. The obtained results are shown in FIGS. 8 and 9. A series of C-terminal deletion mutants are shown in FIG. 8. A series of N-terminal deletion mutants and a series of both-sided C-terminal and N-terminal deletion mutants are shown in FIG. 9. In the FIG. 8, Lanes from Lane 1 to Lane 9 were wild-type (WT), dC50, dC76, dC91, dC157, dC163, dC182, dC213 and GST-dC213 in this order, when electrophoresis was conducted. Their molecular weights were about 4 OkDa, 37 kDa, 36 kDa, 35 kDa, 28 kDa, 26 kDa, 23 kDa, 19 kDa and 42 kDa, respectively. In the FIG. 9, Lanes from Lane 1 to Lane 9 were wild-type (WT), dN41, dN81, dN121, dN161, GST-dN81dc182, GSTdN41dC213, GST-dN81dC213 and GST in this order, when electrophoresis was conducted. Their molecular weights are about 40 kDa, 36 kDa, 32 kDa, 28 kDa, 22 kDa, 36 kDa (a band appearing just left side of Lane 7), 37 kDa, 33 kDa and 28 kDa, respectively.

EXAMPLE 14

(Identification of E3330-binding Domain Using Mutational Recombinant Proteins of Ref-1)

Figure 10:
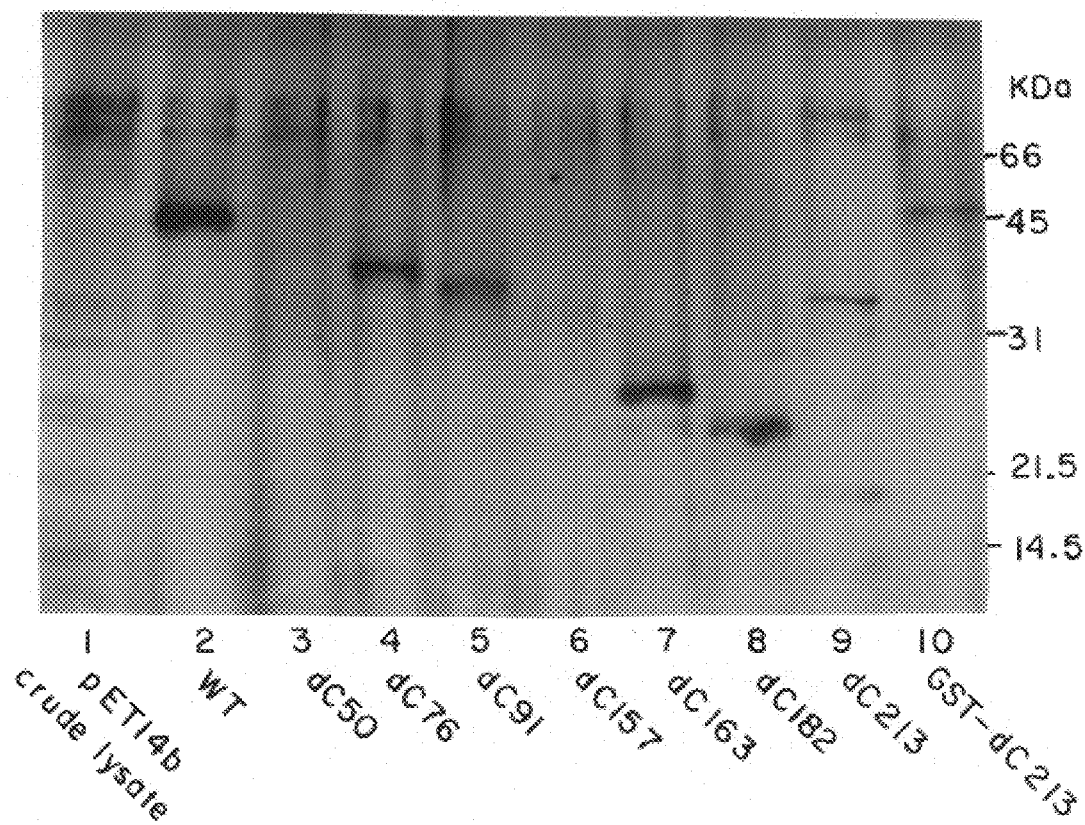
FIG. 10 shows the results of identification of E3330-binding domain using the recombinant proteins of Ref-1 expressed by various deletion mutants.
Figure 11:
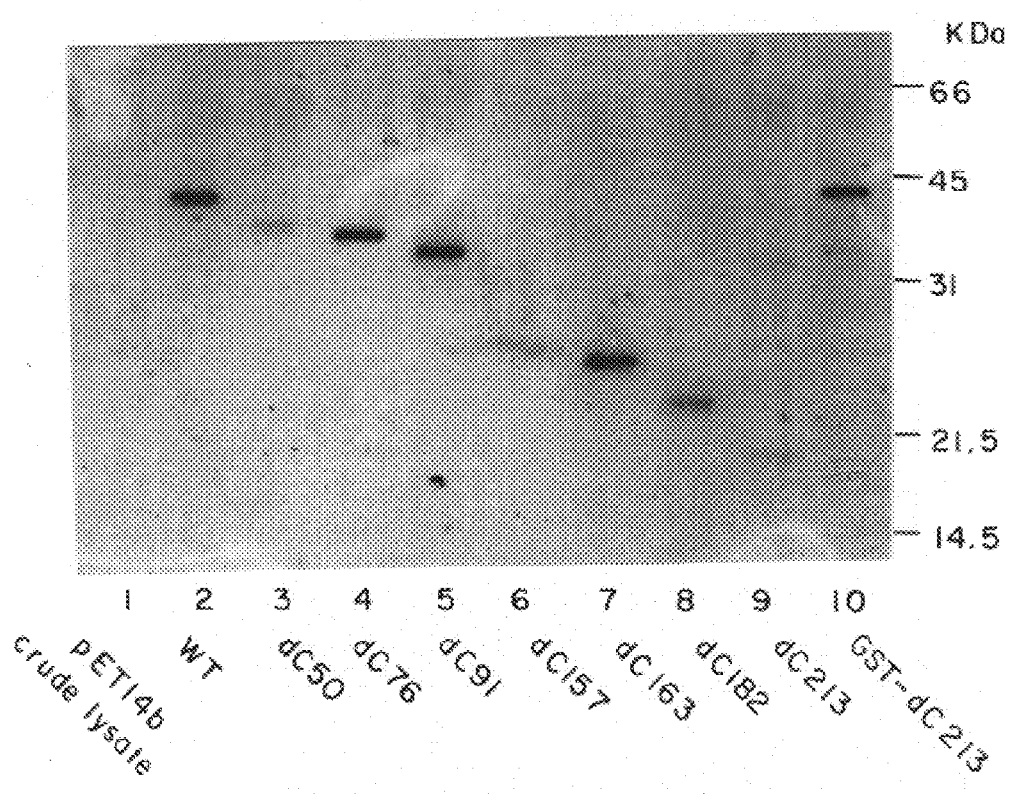
FIG. 11 shows the results of identification of E3330-binding domain using the recombinant proteins of Ref-1 expressed by various deletion mutants.

Which kinds of Ref-1 deletion mutant proteins were bound to E3330 was investigated to identify E3330-binding domain. Therefore, binding assays were performed using E3330-immobilized SG particles. The experimental scheme was the same as illustrated in the FIG. 2. Concerning the elution procedure, two kinds of processes were conducted in this experiment. One is that 2 µg of each purified Ref-1 deletion mutant protein was mixed with E3330-immobilized SG particles, followed by standing still for 30 minutes in an ice-water bath; the protein binding to the particles was eluted with an elution buffer containing 1 M KCl; and then, each eluate was subjected to 12.5% SDS-PAGE and existence of proteins was detected by silver staining. The other one is that 2 µg of each purified Ref-1 deletion mutant protein was mixed with E3330-immobilized SG particles, followed by standing still for 30 minutes in an ice-water bath; 1×SDS sample dye was added to the particles to which each kind of proteins was bound; and the resultant suspension was directly boiled so that the protein binding to the particles was eluted; and then, each eluate was subjected to 12.5% SDS-PAGE and existence of proteins was detected by CBB staining. As a result, it was suggested that the following recombinant deletion mutant proteins of Ref-1 were bound to E3330-immobilized SG particles. In a process using an elution buffer containing 1 M KCl, the binding proteins were wild-type (about 40 kDa), dC76 (about 36 kDa), dC91 (about 35 kDa), dC163 (about 26 kDa), dC182 (about 23 kDa), dC213 (about 19 kDa) and GST-dC213 (about 42 kDa). In the other process using a direct boiling method, the binding proteins were wild-type (about 40 kDa), dN41 (about 36 kDa), dN81 (about 32 kDa), GST-dN81dC182 (about 36 kDa) and GST-dN81dC213 (about 33 kDa). These obtained results are shown in FIGS. 10 and 11.

Figure 12:
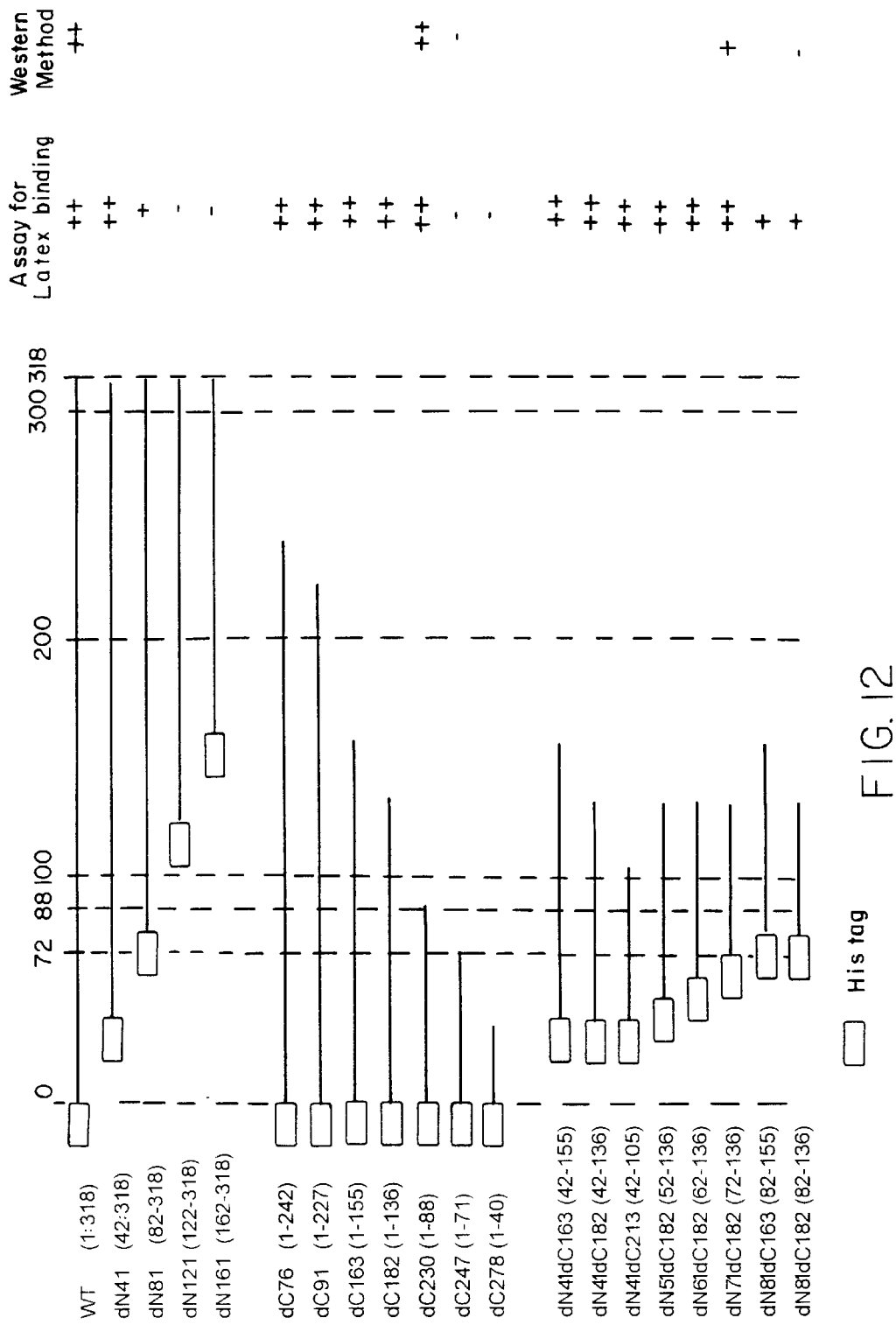
FIG. 12 shows the summary of E3330-binding domain in Ref-1 identified using the recombinant proteins of Ref-1 expressed by various deletion mutants.

From the above results, Ref-1, that is a protein consisting of 318 amino acid residues in its whole length, does not bind to-E3330 in case where 231 or more amino acid residues from its C-terminus are deleted or in case where 72 or more amino acid residues from its N-terminus are deleted. Therefore, it was revealed that the amino acid sequence of at least 72 a.a. to 88 a.a. participated in the binding activity of Ref-1 against E3330, as shown in FIG. 12. Actually, recombinant protein possessing only the concerned amino acid sequence (72 a.a. to 88 a.a.) was synthesized and investigated on its binding properties using E3330-immobilized particles, resulting in confirmation of its binding ability against E3330. The amino acid sequence of 72 a.a. to 88 a.a. is as follows SEQ ID NO:13; length of sequence: 17 amino acids): LRAWIKKKGLDWVKEEA.

These results indicated that the intracellular receptor to E3330 was isolated and purified using E3330-immobilized particles and it is clear that the present invention is extremely useful for isolation and purification of proteins.

EXAMPLE 15

(Immobilization of DM852 to SG-EGDE Particles)

Five mg of SG-EGDE particles, were prepared as described above, was washed three times with 1 ml of $DH_2O$. After washing, 500 µl of $DH_2O$ solution containing 5 µmol of DM852 was added to the packed SG-EDGE, followed by reaction at 37° C. for 24 hours, in order to immobilize DM852 to epoxy groups of EGDE on the surfaces of SG-EGDE particles. After the reaction was finished, the particles were washed three times with 500 µl of $H_2O$. The drug-immobilized particles were stored at 4° C. in a dark place with 500 µl of $H_2O$. The centrifugation procedure for washing was conducted at 12,000×g for 3 minutes at room temperature. Under these reaction conditions about 0.1 mmol of DM852 was immobilized onto 1 g of the SG-EGDE particles. The above immobilized amount of DM852 was obtained by subtracting the amount of DM852 not bound to the SG-EGDE particles frown the starting amount of DM852. DM852 shows the maximum absorption at the wave-length of 265.0 nm, so that each amount of DM852 can be determined by measuring an absorbance at the wave-length of 265.0 nm on each sample; such as the starting solution, not binding fraction and washing fractions. The measurement on the absorbance was conducted with DU-64 Spectrophotometer (BECKMAN).

(Preparation of a Crude Nuclear Extract, Cytoplasmic and Membrane Fractions)

The culture of LP101 stroma cells, (5×10$^8$ cells), which were cultured in a 150 mm dishes, was scraped and the collected cells was conducted using 15-ml-centrifugation tubes and washed two times with PBS(−) at 300×g; for 5 minutes at 4° C. Then, the final packed cell volume (PCV) was measured. Buffer A (10 mM Tris-HCl pH 7.4, 1 mM MgCl$_2$ 1 mM EDTA, 0.5 mM DTT, 1 mM PMSF, 1 μgl/ml pepstain A, 1 μgl/ml leupeptin), four times larger volume of the PCV, was added to the packed cells to suspend the cells. The cell suspension was allowed to stand still on ice for 10 minutes so that the cells were swollen. The cell membranes of the swollen cells were broken by 20 strokes using a 15-ml-B-type Dounce homogenizer (IWAKI), transferred to 15-ml-centrifugation tubes (IWAKI) and add NaCl (final concentration 0.15M). Then, it was centrifuged at 840×g for 10 minutes at 4° C. for the purpose of separating a nuclear fraction (pellet) from a membrane and cytoplasmic fraction (supernatant).

Buffer A, five times more volume of the PCV, was added to the isolated nuclear fraction to re-suspend the nuclei. The nuclear suspension was centrifuged at 4,000×g for 5 minutes at 4° C. for the purpose of removing the contaminated cytoplasmic fraction. The obtained nuclear pellet was dispersed In Buffer C (20 mM Tris-HCl pH 7.4, 420 mM NaCl$_2$ 1 mM MgGl$_2$, 0.2 mM EDTA, 10%(v/v)glycerol, 0.5 mM DTT, 1 mM PMSF, 1 μg/ml pepstatin A, 1 μg/ml leupeptin), the same volume as the PCV, and thoroughly suspended by 10 strokes using a B-type Dounce homogenizer. The suspension was slowly stirred for 30 minutes at 4° C. for the purpose of extracting nuclear components. The extract was transferred to a 15-ml-centrifugation tube and centrifuged at 12,000×g for 30 minutes at 4° C. The obtained supernatant was dialyzed two times against 500 ml of Buffer E (10 mM Tris-HCl pH 7.4, 100 mM NaCl$_2$ 1 mM MgCl$_2$, 1 mM CaCl$_2$, 0.2 mM EDTA, 10%(v/v)) glycerol, 0.1% NP-40, 0.5 mM DTT, 1 mM PMSF, 1 μg/ml pepstatin A, 1 μgl/ml leupeptm) for 6 hours at 4° C.

On the other hand, the cytoplasmic fraction was, transferred to an ultra-centrifugation tube (BECKMAN NO: 344057) and ultra-centrifuged at 100,000×g for one hour at 4° C. (BECKMAN: Rotor Type SW50. 1) for the purpose of separating a membrane (pellet) from a cytoplasmic fraction (supernatant).

The obtained cytoplasmic fraction was dialyzed in the same manner as the above procedure for the nuclear extract.

Buffer A, two times more volume of the PCV, was added to re-suspend the obtained membrane fraction and Octyl-glucoside (final concentration 3%) was added for the purpose of solubilizing the membrane fraction. The suspension was slowly stirred for four hours at 4° C., and ultra-centrifuged at 100,000×g for one hour at 4° C. (BECKMAN: Rotor Type SW50. 1). Then, the solubilized membrane fraction was dialyzed in the same manner as the above procedure for the nuclear extract.

After the completion of the dialyses, the nuclear extract, the cytoplasmic fraction and the membrane fraction even subdivided into appropriate aliquots and stored at −80° C. until the use of them.

In usual preparation, about 5 ml (5 mg/ml) of the nuclear extract 15 ml (3 mg/ml) of the cytoplasmic fraction and 15 ml (2 mg/ml) of the membrane fraction, respectively were obtained in the scale of this working example.

(Isolation of Proteins Using Microspheres)

Microspheres and the extract and each fraction were mixed and centrifuged to separate substances binding to DM852 which was immobilized on particles from the mixture. The centrifugation procedure for separation was conducted at 12,000×g for 3 minutes at 4° C. All procedures in the above were conducted at 4° C.

First, 1 mg of each DM852-not-immobilized SG-EGDE particles and DM-852-immobilized SG-EGDE particles mixture, which include 0.03 mg of DM852-immobilized SG EGDE particles, were washed three times with 400 μl of Buffer E. These particles were used as a reference control against DM852 immobilized SG EGDE particles. To these washed particles DM852-not immobilized SG EGDE and DM852-immobilized SG-EGDE particles mixture, 500 μl each of the extract and fractions, were added and mixed. These mixtures were allowed to be standing still for 4 hours with intermittently rotating in order to bind proteins possessing DM852-binding abilities to DM852 which was immobilized on the particles. The mixture was centrifuged and the supernatant was discarded. The pellet was washed three times with 500 μl of Buffer E to remove non-specific binding substances as much as possible. Subsequently the washed pellet was eluted with 50 μl of Buffer E+ which contained 10 mM DM852 in Buffer E, so that the proteins possessing DM852-binding abilities were dissociated and eluted from DM852 immobilized on the particles. The washed solution and eluted solution were stored at −80° C.

The detection of the proteins possessing DM852-biinding abilities was conducted by electrophoresis on a 10% SDS-polyacrylamide gel (SDS-PAGE) using 5 μl obtained from the DM852-immobilized SG-EGDE particles mixture and DM852-not-immobilized SG-EGDE particles used as a reference control. In this experiment, 4×SDS special dye (200 mM Tns-HCl(pH 6.8), 500 mM β-mercaptoethanol (β-ME), 8% SOS, 0.4% BPB) was used instead of 4×SDS sample dye in order to prevent the electrochoresis from being disordered due to such high concentration of the salts. The electrophoresed gel was subjected to silver staining and the proteins specifically binding to DM852 were identified in comparison with the results of the reference control. As a result, in the membrane fraction, two protein bands with molecular weights of about 70 kDa aloud 80 kDa which were not observed in the reference control were clearly observed, suggesting that the proteins were specifically binding to DM852. The DM852-binding proteins were obtained about 10 ng each in the above procedure. In the nuclear extract and cytoplasmic fractions any specific bands were not detected.

(Evaluation of Specific-binding Abilities Against DM852)

To confirm that the protein was specifically bound to DM852 a competitive binding-inhibitory experiment was conducted.

In the step of the above procedure for the addition of the membrane fraction to SG-EGDF particles, free DM852 at 100 times and 400 times more moles of the DM852 immobilized on the particles were added simultaneously. Then, the protein possessing specifically binding abilities to DM852 immobilized on the particles would be bound to free DM852, resulting in a lower yield in the isolation using the particles. As a result, it was confirmed that the yield of the protein with a molecular weight of about 70 kDa and 80 kDa were lowered, indicating that the proteins were specifically bound to DM852.

EXAMPLE 16
(Immobilization of H-9 with a Spacer)

The spacer-immobilized particles, that are SG-EGDE, particles, were prepared as described above. Five mg of SG-EGDE particles were washed with 200 µl of $H_2O$ three times and then 500 µl of H20 containing H-9 (final conc. 30 mM) was added to the particles in order to immobilize H-9 to epoxy group of EGDE on the surface of SG-EGDE particles. After 12 hours incubation at 37° C. in a dark room, the particles were washed three times with 400 µl of $H_2O$ through a centrifugation manner. Then, the particles were dispersed in 0.5 M Tris-HCL buffer (pH 8.5), allowed to be standing still 4° C. for at least 24 hours and used in order to thoroughly mask the intact epoxy groups, on the surface of SG-EGDE particles. The drug-immobilized particles were stored at 4° C. in a dark place. The centrifugation procedure for washing was conducted at 15,000×g for 5 minutes at room temperature. Under these reaction conditions about 0.14 mmol of H-9 was immobilized onto 1 g of the SG-EGDE) particles.

(Isolation of Proteins Using Microspheres)

HeLa cell nuclear extracts (NE) were prepared according to the method as described previously (Dignam,J. D., Lebovitz,R. M. and Roeder, R. G. (1983). Accurate transcription by RNA pol II in a soluble extracts from isolated mammalian nucleic. Nucleic Acids Res 11. 1475–1489). Three hundred micrometer of NE was incubated for 30 minutes at 4° C. with 1.0 mg of H-9-not-immobilized SG-EGDE particles and H-9-immobilized SG-EGDE particles which have been washed three times with 200 µl of HGKEDN (20 mM HEPES (pH 7.9), 10% (V/V) glycerol, 0.1M KCL, 0.2 mM EDTA, 1 mM DTT, 0.1% Nonidet P-40(NP-40)). The H9-not-immobilized SG.EGDE particles were dispersed in 1 ml of 1 M Tris HCl buffer solution (pH 7.4) and allowed to be standing still at 4° C. for at least 24 hours in order to mask epoxy groups of EGDE. These particles were used as a reference control against H-9-immobilized SG EGDE particles. The mixture was centrifuged and the supernatant was discarded. The pellet was washed three times with 500 µl of HGKEDN to remove non-specific binding substances as much as possible.

Subsequently, the washed pellet was eluted three times with HGKEDN containing 1 M KCl or 3 mM H-9 or 3 mM H-9, so that the proteins possessing H-9-binding abilities were dissociated and eluted from H-9 is immobilized on the particles. The wash solution and eluate solution were stored at −80° C.

The detection of the proteins possessing H9-binding abilities was conducted by electrophoresis on a 10% SDS-polyacrylamide gel (SDS-PAGE) using 20 µl each of the first, second or third eluate solution obtained from the H-9-immobilized SG-EGDE particles and H9-not-immobilized SG EGDE particles used as a reference control. In this experiment, 4×SDS special dye (200 mM Tns-HCl pH 6.8), 500 mM b-mercaptoethanol (b-ME), 8% SDS, 0.4% BPB) was need instead of 4×SDS special dye in order to prevent the electrophoresis from being disordered due to such high concentration of the salts. The electrophoresed gel was subjected to silver staining and the protein specifically binding to H-9 were identified in comparison with the results of the reference control. As a result, a protein band with a molecular weight of about 30 kDa which was not observed in the reference control was clearly observed, suggesting that the protein was specifically binding to H-9. The same protein band was obtained by elution using H-8 or H-9, suggesting that the 30 kDa protein was bound to the H-9-immobilized SG-EGDE particles in a specific manner.
(Evaluation of Specific Binding Abilities Against H-9)

A competition experiment was conducted to confirm that the protein with a molecular weight of about 30 kDa in HeLa cell nuclear extract was specifically bound to H-9. In the step of a procedure for the addition of HeLa cell nuclear extracts to SG-EGDE particles, when free H-9 or H-8 were added simultaneously to H-9-immobilized SG-EGDE particles with indicated concentrations, the addition of the drugs resulted in a lower yield of the 30 kDa protein in the isolation using the particles. Thus, it was confirmed that the yield of the protein with a molecular weight of About 30 kDa was lowered, indicating that the protein was specifically bound to H-9 or H.8.

EXAMPLE 17
(Immobilization of an Amino Derivative of DQ2511 (Ecabapide) with a Spacer)

(a) (Induction of an amino derivative of DQ2511)

As DQ2511 does not possess an appropriate functional group, it is difficult to immobilize DQ2511 onto SG-EGDE particles. Therefore, $NH_2$-DQ2511 was synthesized through the induction of an amino group into DQ2511.

(b) (Immobilization of $NH_2$-DQ2511 to SG-EGDE particles)

Ten mg of SG-EGDE particles described above was washed three times with 500 µl of $H_2O$ through a centrifugation procedure. After washing, 500 µl of $H_2O$ solution containing 4 µmol of $NH_2$-DQ2511 was added to the packed SG-EGDE particles to disperse the SG-EGDE particles in the above solution, followed by reaction at 37° C. for 24 hours, in order to immobilize $NH_2$-DQ2511 to epoxy groups of EGDE on the surfaces of SG-EGDE particles. After the reaction was finished, the particles were washed three times with 400 µl of $H_2O$ through a centrifugation procedure. Then, the particles were dispersed in 500 µl of 0.5 M Tris-HCl buffer solution (pH 8.5), allowed to be standing still at 4. C. for at least 24 hours and used, in order to thoroughly mask the intact epoxy groups on the surfaces of SG-EGDE particles. The drug-immobilized particles were stored at 4° C. in a dark place. The centrifugation procedure for washing was conducted at 15,000×g for 5 minutes at room temperature. Under these reaction conditions about 0.06 mmol of $NH_2$-DQ2511 was immobilized onto 1 g of the SG-EGDE particles. The above immobilized amount of $NH_2$-DQ2511 was obtained by subtracting the amount of $NH_2$-DQ251 not bound to the SG-EGDE particles from the starting amount of $NH_2$-DQ2511 $NH_2$-DQ2511 shows the maximum absorption at the wave-length of 275.0 nm, so that each amount of NH2-DQ2511 can be determined by measuring an absorbance at the wave-length of 275.0 nm on each sample, such as the starting solution, not-binding fraction and washing fractions. The measurement on the absorbance was conducted with DU-64 Spectrophotometer (BECKMAN).
(Preparation of a Crude Cytoplasmic Fraction from HeLa Cell)

The culture medium suspension of HeLa cells ($3 \times 10^9$ cells), which were cultured in a suspension scale of 8 liters, was centrifuged using 500-ml-centrifigation tubes (NARGEN) at 500×g for 10 minutes at 4° C. for the purpose of collecting the cells. The collected cells were washed two times with PBS(−). The washing procedure was conducted using 50-ml-centrifugation tubes and the centrifugation conditions were At 700×g for 5 minutes at 4° C. Then, the final packed cell volume (PCV) was measured. Buffer A (10 mM Hepes pH 7.9, 1.5 mM MgCl$_2$, 10 mM KCl, 0.5 mM DTT), four times larger volume of the PCV, was added to the packed cells to suspend the cells. The cell suspension was allowed to stand still on ice for 20 minutes 90 that the cells were swollen. The cell membranes of the swollen cells were broken by 20 strokes using a 40-ml-B-type Dounce homogenizer (WHEATON), transferred to a 50-ml-centrifugation tube (NARGEN) and centrifuged at 4,200×g for 6 minutes at 4° C. for the purpose of separating a nuclear fraction (pellet) and a cytoplasmic fraction (supernatant).

The cytoplasmic fraction was transferred to a 50-ml-centrifugation tube and centrifuged at 20,000×g for 1 hour at 4° C. The obtained supernatant was dialyzed three times against 500 ml of Buffer 0.05 HKMGED (20 mM Hepes pH 7.9, 10% (V/V) glycerol, 0.05 M KCl, 1 mM MgCl$_2$, 0.2 mM EDTA, 0.4 mM PMSF, I mM DTT) for 2 hours at 4° C. After the completion of the dialyses, the cytoplasmic fraction of HeLa cell was centrifuged at 20,000×g for 1 hour at 4° C. The obtained supernatants was used as the sample of cytoplasmic fraction of HeLa cell. This sample was subdivided into appropriate aliquots and stored at −80° C. until the use of them. In usual preparation, about 20 ml of the cytoplasmic fraction at the protein concentration of 10 mg/ml, was obtained in the scale of this working example,
(Preparation of a Crude Lysate from Rat Dorsal Root Ganglia (DRG) Cell)

Dorsal root ganglia cells isolated from rats were washed two tines with PBS(−). The washing procedure was conducted using 15-ml-centrifugation tubes and the centrifugation conditions were at 700×g for 5 minutes at 4° C. Then, the final packed cell volume (PCV) was measured, PBS(−), four times larger volume of the PCV, was added to the packed cells to suspend the cells. The cells were broken completely by homogenize, transferred to 1.5 ml tubes (eppendorf) and centrifuged at 136,000×g for 1 hour at 4° C. In usual preparation, the supernatant of lysate including 1 mg/ml of protein was obtained.

To concentrate the crude lysate of DRG cell, the proteins contained in it were salted out with saturated ammonium sulfate. After centrifugation at 20,000×g for 1 hour at 4° C., the supernatant was removed. The pellet was dissolved with 0.05 HKMGED (20 mM Hepes pH 7.9, 10% (V/V) glycerol, 0.05 M KCl, 1 mM MgCl$_2$, 0.2 mM EDTA, 0.4 mM PMSF, 1 mM DTT) to be one fourth volume of starting lysate. The concentrated lysate was dialyzed three times against 500 ml of Buffer 0.05 HKMGED (20 mM Hepes pH 7.9, 10% v/v) glycerol, 0.05 M ACT, 1 me MgClz, 0.2 mM EDTA, 0.4 MU PMSF, 1 EM DTT) for 2 hours at 4° C.

After the completion of the dialyses, the concentrated lysate of DRG cell was centrifuged at 20,000×g for 1 hour at 4° C. The obtained supernatant was used as the sample of lysate of DRG cell. This sample was subdivided into appropriate aliquotd and stored at −800° C. until the use of them. In usual preparation, the concentrated lysate including 3 mg/ml of protein was obtained
(Isolation of Proteins from a Cytoplasmic Fraction of HeLa Cell Using Microspheres)

A process of isolation and purification of DQ251 1-binding proteins using DQ251 1-immobilized particles is illustrated above. Before using, cytoplasmic fraction of HeLa cell was diluted to ten third volume with Buffer 0.05 HKMGEDN (20 mM Hepes pH 7.9, 10% v/v glycerol, 0.05 M KCl, 1 mM MgCl:, 0.2 mM EDTA, 0.4 mM PMSF, 1 mM DTT, 0.01% NP-40).

(a) microspheres and the diluted cytoplasmic fraction were mixed and centrifuged to separate substances binding to DQ2511 which was immobilized on particles from the mixture. The centrifugation procedure for separation was conducted at 15,000×g for 5 minutes at 44° C. All procedures in the above were conducted at 4° C.

(b) First, 1 mg each of DQ2511-not-immobilized SG-EGDE particles and DQ2511-immobilized SG-EGDB particles were washed three times with 400 μl of Buffer 0.05 HKMGEDN (20 mM Hepes pH 7.9, 10% (V/V) glycerol, 0.05 M KCl, 1 mM MgCl$_2$, 0.2 mM EDTA, 0.4 mM PMSF, 1 mM DTT, 0.01% NP-40). The DQ2511-not-immobilized SG-EGDE particles were dispersed in 1 ml of 0.5 M Tris-HCl buffer solution (pH 8.5) and allowed to be standing still at 4° C. for at least 24 hours in order to mask epoxy groups of EGDE. These particles were used as a reference control against DQ2511-immobilzed SG-EGDE particles. To these washed DQ2511-not-immobilized SG-EGDE particles and DQ2511-immobilized-SG-EGDE particles, 1 ml of the diluted cytoplasmic fraction was added and mixed. These mixtures were rotated for 1 hour at 4° C. in order to bind proteins possessing DQ2511-binding abilities to DQ2511 which was immobilized on the particles. The mixture was centrifuged and the supernatant was discarded. The pellet was washed seven times with 200 μl of 0.05 HKMGEDN to remove non-specific binding substances as much as possible. Subsequently, the washed pellet was eluted two times with 20 μl of Buffer 1.0 HKMGEDN (20 mM Hepes pH 7.9, 10% (v/v) glycerol, 1.0 M KCl, 1 mM MgCl$_2$, 0.2 mM EDTA, 0.4 mM PMSF, 1 mM DTT, 0.01% NP-40), so that the proteins possessing DQ2511-hinding abilities were dissociated and eluted from DQ2511 immobilized on the particles. The wash solution and eluate solutions were stored at −80° C.

(c) The detection of the proteins possessing DQ2511-binding abilities were conducted by electrophoresis on a 8% SDS-polyacrylamide gel (SDS-PAGE) using 5 μl each of the first, second or third eluate solution obtained from the DQ2511-immobilized SG-EGDE particles and DQ2511-not-immobilized SG-EGDE particles used as a reference control. The electrophoresed gel was subjected to silver staining and the proteins specifically binding to DQ2511 were identified in comparison with the results of the reference control. As a result, in the cytoplasmic fraction a protein band with a molecular weight of about 110 kDa which was not observed in the reference control was clearly observed, suggesting that the protein was specifically binding to DQ2511.

In the above procedure, about 20 ng of 110 kDa DQ2511-binding protein as obtained from 1 mg of the DQ2511-immobilized SG-EGDE particles.
(Isolation of Proteins from a Lysate of Rat DRG Cell Using Microsphere)

Microspheres and the concentrated crude lysate of rat DRG cell were mixed and centrifuged to separate substances binding to DQ2511 which was immobilized on particles from the mixture. The procedures of binding, washing and detection of protein were performed as described above. As a result, a protein with a molecular weight about 170 kDa was obtained as the protein possessing DQ2511-binding ability. In the above procedure, about 10 ng of 170 kDa DQ2511-binding protein was obtained from 1 mg of the DQ2511-immobilized SG-EGDE particles.
(Evaluation of Specific-binding Abilities Against DQ2511)

The following competitive binding-inhibitory experiment was conducted to confirm that the 110 kDa protein in the cytoplasmic fraction of HeLa cell and 170 kDa protein in the lysate of rat DRG cell bound to DQ2511 specifically.

When in the step of a procedure for the addition of either the cytoplasmic fraction or crude lysate of rat DRG cell to SG-EGDE particles, free $NH_2$-DQ2511 at 50 times, 150 times or 500 times more moles than the immobilized $NH_2$-DQ2511 were added simultaneously. The protein possessing specifically binding abilities to DQ2511 immobilized on the particles would be bound to free $NH_2$-DQ2511, resulting in a lower yield in the isolation using the particles. As a result, the purifications of the protein with a molecular weight of about 110 kDa and the protein with a molecular weight of about 170 kDa from the DQ2511-immobilized particles were inhibited with dose dependence of free $NH_2$-DQ2511, indicating that the proteins were specifically bound to $NH_2$-DQ2511.

EXAMPLE 18
(Immobilization of KF43389 to SG-EGDE Particles)

Five mg of SG-EGDE particles was washed three times with 1 ml of 1.4-dioxane through a centrifugation procedure. After washing, 500 µl of 1.4-dioxane solution containing 15 µmol of KF49389 was added to the packed SG-EGDE particles to disperse the SG-EGDE particles in the above solution, followed by reaction at 37° C. for 48 hours, in order to immobilize KF49389 to epoxy groups of EGDE on the surface of SG-EGDE particles. After the reaction was finished, the particles were washed three times with 500 µl of 1.4-dioxane and three times with water through a centrifugation procedure. The drug-immobilized particles were stored at 4° C. in a dark place with 500 µl of water. The centrifugation procedure for washing was conducted at 15,000×g for 5 minutes at room temperature under these reaction conditions about 0.15 mmol of KF49389 was immobilized onto 1 g of the SG-EGDE particles. The above immobilized amount of KF49389 was obtained by subtracting the amount of KF49389 not bound to the SG-EGDE particles from the starting amount of KF49389. KF49399 shows the maximum absorption at the wave-length of 282.0 nm so that each amount of KF49389 can be determined by measuring an absorbance at the wave-length of 282.0 nm on each sample, such as the starting solution, not-binding fraction and washing fractions. The measurement on the absorbance was conducted with DU-64 Spectrophotometer (BECKMAN).

(Preparation of a Crude Nuclear Extract and a Cytoplasmic Fraction)

The culture of MG63 cells ($1 \times 10^9$ cells), which were cultured in a 150 mm dishes, was scraped and the collected cells was conducted using 50-ml-centrifugation tubes and washed two times with PBS(−) at 3000×g for 10 minutes at 4° C. Then, the final packed cell volume (PCV) was measured. Buffer A (10 mM Hepes pH 7.9, 1.5 mM $MgCl_2$, 10 mM KCl, 0.5 mM DTT), two times larger volume of the PCV, was added to the packed cells to suspend the cells. The cell suspension was allowed to stand still on ice for 10 minutes so that the cells were swollen. The cell membranes of the swollen cells were broken by 20 strokes using a 40-ml-B-type Dounce homogenizer (WHEATON), transferred to a 50-ml-centrifugation tube (NARGEN) and centrifuged at 2000×g for 10 minutes at 4° C. for the purpose of separating a nuclear fraction (pellet) from a cytoplasmic fraction (supernatant). Buffer A, five times larger volume of the PCV, was added to the isolated nuclear fraction to re-suspend the nuclei. The nuclear suspension was centrifuged at 4,200×g for 6 minutes at 4° C. for the purpose of removing the contaminated cytoplasmic fraction. The obtained nuclear pellet was dispersed in Buffer C (20 mM Hepes pH 7.9, 25% v/v glycerol, 0.42 M NaCl, 1.5 mM $MgCl_2$, 0.2 mM EDTA, 0.5 mM PMSF, 1 mM DTT), the same volume as the PCV, and thoroughly suspended by 10 strokes using a B-type Dounce homogenizer. The suspension was slowly stirred for 30 minutes at 4° C. for the purpose of extracting nuclear components. The extract was transferred to a 50-ml-centrifugation tube and centrifuged at 3,000×g for 10 minutes at 4° C. The obtained supernatant was dialyzed two times against one liter of Buffer D (20 mM Hepes pH 7.9, 10% (V/V) glycerol, 0.05 M KCl, 0.2 mM EDTA, 1 mM $MgC_2$, 0.1 mM PMSF, 1 mM DTT) for 4 hours at 4° C.

On the other hand, the cytoplasmic fraction was transferred to an ultra-centrifugation tube and ultra-centrifuged at 35 Krpm for one hour at 4° C. (BECKMAN: Rotor Type SW: 50.1). The obtained supernatant was dialyzed in the same manner as the above procedure for the nuclear extract.

After the completion of the dialyses, the nuclear extract and the cytoplasmic fraction were subdivided into appropriate aliquots and stored at −80° C. until the use of them.
(Isolation of Proteins Using Microspheres)

(a) Microspheres and the cytoplasmic were mixed and centrifuged to separate substances binding to KF49389 which was immobilized on particles from the mixture. The centrifugation procedure for separation was conducted at 15,000×g for 5 minutes at 4° C. All procedures in the above were conducted at 4° C.

(b) First, 0.5 mg each of KF49389-not-immobilized SG-EGDE particles and KF49309-immobilized SG-EGDE particles were washed three times with 400 µl of Buffer D. These particles were used as a reference control against KF49389-immobilized SG-EGDE particles. To these washed KF49389-not-immobilized SG-EGDE particles and KF49389-immobilized SG-EGDE particles, 3 mg per 1 ml of the cytoplasmic fractionation, was added and mixed. These mixtures were allowed to be standing still for 4 hours with rotating in order to bind proteins possessing KF49389-binding abilities to KF49389 which was immobilized on the particles. The mixture was centrifuged and the supernatant was discarded. The pellet was washed four times with 500 µl of Buffer D to remove non-specific binding substances as much as possible.

Subsequently, the washed pellet was eluted with 30 µl of Buffer E (20 mM Hepes pH 7.9, 10% (V/V) glycerol, 1 mM DTT, 0.2 mM EDTIA, 1 mM $MgCl_2$, 0.1 mM PMSF 1 mM DTT), so that the proteins possessing KF49389-binding abilities were dissociated and eluted from KF49389 immobilized on the particles. The wash solution and eluate solution were stored at −80° C.

(c) The detection of the proteins possessing KF49389-binding abilities was conducted by electrophoresis on a 10% SDS-polyacrylamide gel (SDS-PAGE) using 10 µl obtained from the KF49389-immobilized SG-EGDE particles and KF49389-not-immobilized SG-EGDE particles used an a reference control. In this experiment, 4×SDS special dye (200 mM Tris-HCl (pH 6.8), 500 mM β-mercaptoethanol (β-ME), at SDS, 0.4% BPB) was used instead of 4×SDS sample dye in order to prevent the electrophoresis from being disordered due to such high concentration of the salts. The electrophoresed gel was subjected to silver staining and the proteins specifically binding to KF49389 were identified in comparison with the results of the reference control. As a result, in the cytoplasmic fraction a protein band with a molecular weight of about 55 kDa which was not observed in the reference control was clearly observed, suggesting that the protein was specifically binding to KF49389. This binding protein was obtained about 10 ng from each tubes.
(Confirmation of the Binding Ability of KF49389-binding Protein)

(a) The above procedure was repeated and finally 5 μg of KF49389-binding protein was obtained. N-terminal amino acid sequence of the obtained protein was analyzed and three different sequences was detected. These amino acid sequences were analyzed using a computer and determined to be identical with the amino acid sequences of N-terminal region of three different proteins. These proteins are conditionally named as protein A, B. C, respectively, These proteins were cloned using PCR method from HeLa cells cDNA library, and subcloned into E. coli expression plasmids pGEX4T-2 (Pharmacia) which would express the GST-Tag fused recombinant protein of A, B, C wild type. The expression plasmids were introduced into E. coli BL21 (DE3) and protein expression was induced by addition of 0.4 mM IPTG. Purification of the GST-tagged proteins was performed according co the manufacturer's instructions (Pharmacia}.

(b) The binding ability of the recombinant protein obtained in the above procedure against KF49389 was investigated using KF49389 immobilized particles 400 ng per 500 μl of the recombinant protein, GST alone or GST-Tagged protein A, B, C, was incubated with KF49389 immobilized particles and performed as above, As a result, GST alone was not recovered from KF49389-immobilized particles, entirely. In contrast, recombinant proteins of GST-Tagged protein A, B, C were recovered from KF49389-immobilized particles and especially GST-Tagged A was obtained high efficiently against input recombinant protein (about 80%). These results indicates that the protein A, B, C can bind with KF49389 specifically and the protein A has a high affinity with KF49389.

EXAMPLE 19
(Isolation of Proteins Using Microspheres)

Figure 14:
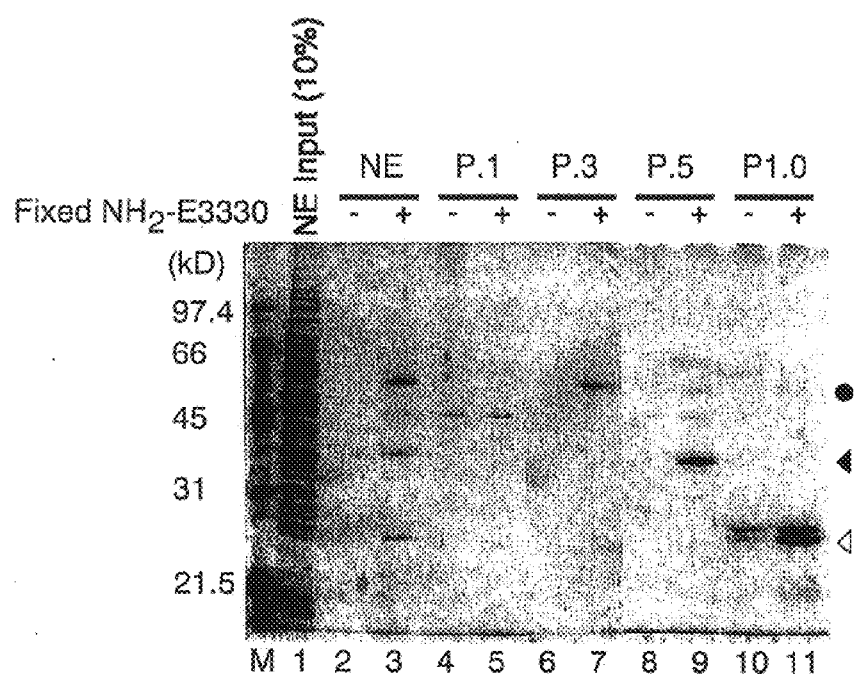
FIG. 14 shows the isolation and purification of E3330-binding proteins using E3330-immobilized particles.
Figure 15:
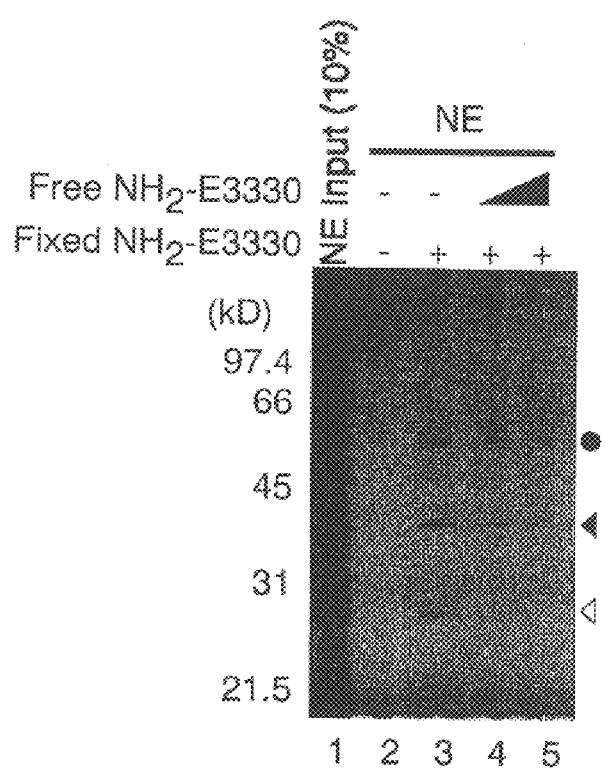
FIG. 15 shows the isolation and purification of E3330-binding proteins using E3330-immobilized particles.

A process of isolation and purification of E3330-binding proteins using E3330-immobilized particles is illustrated in FIGS. 14 an 15.

(a) Microspheres and the crude nuclear extract or each fraction obtained through the fractionation use a phosphocellulose column in the working example 5 were mixed and centrifuged to separate substances binding to E3330 which was immobilized on particles from the mixture. The centrifugation procedure for separation was conducted at 15,000×g for 5 minutes at 4° C. All processes in the above were conducted at 4° C.

(b) First, 1 mg each of E3330-not-immobilized SG-EGDE particles and E3330-immobilized SG-EGDE particles were washed three times until 250 μl of Buffer D2 (20 mM HEPES (pH 7.9), 10% (V/V) glycerol, 0.125 M KCL 0 2 mM EDTA, 1 mM DTT) in Which KCl and glycerol concentrations were 0.125 M and 10% instead of 0.1 M and 20%, respectively, in Buffer D. The E3330-not-immobilized SG-EGDE particles were dispersed in 1 ml of 1 M Tris-HCl buffer solution (pH 7.4) and allowed to be standing sell at 4° C. for at least 24 hours in order to mask epoxy groups of EGDE. These particles were used as a reference control against E3330-immobilized SG-EGDE particles To these washed E3330-not-immobilized SG-EGDE particles and E3330-immobilized SG-EGDE particles, 100 μl each of each of the nuclear extract, P. 1, P.3 P.5, or P 1.0 which were diluted with buffer D2 to a concentration of 0.16 mg/ml was added and mixed These mixtures were allowed to be standing still for 30 minutes with intermittenly stirring at intervals of 10 minutes in order to bind proteins possessing E3330-binding abilities to E3330 which was immobilized on the particles. The mixture was centrifuged and the supernatant was discarded. The pellet was washed five times With 250 μl of Buffer D2 to remove non-specific binding substances as much as possible. Subsequently, the washed pellet was eluted with 20 μl of Buffer D containing 1M KCl, so that the proteins possess E3330-binding abilities were disassociated and eluted from E3330 immobilized on the particles. The wash solution and eluate solution were stored at −80° C.

(c) The detection of the protein possessing E3330-binding abilities was conducted by electrophoresis on a 10% SDS-polyacrylamide gel (SDS-PAGE) using 10 μl of the eluate solution obtained from the E3330-mobilized SG EGDE particles and E3330-not-immobilized SG-EGDE particles used as a reference control. In this experiment, 4×SDS Special dye (200 mM Tris-HCl (pH 6.8), 500 mM β-mercaptoethanol (p-ME), 8% SDS, 0.4% BPB) was used instead of 4×SDS sample dye in order to prevent the electrophoresis from being disordered due to such high concentration of the salts. The electrophoresed gel was subjected to silver staining and the proteins specifically binding to E3330 were identified in comparison with the results of the reference control. As a result, from the purification using nuclear extract, three protein bands with a molecular weight of about 60, 38, and 27 kDa which were not observed in the reference control were clearly observed, suggesting that the proteins revere specifically binding to E3330. From the purification using P.1, there was not observed any specific protein band specifically eluted from E3330-immobilized particles.

The above procedure was repeated and finally 5 μg of E3330-binding protein with a molecular weight of about 38 kDa was obtained. From the purification using P.3, a protein band with a molecular weight of about 60 kDa which were not observed in the reference control were clearly observed. From the purification using P.5, a protein hand with a molecular weight of about 38 kDa which were not observed in the reference control were clearly observed. From the purification using P.1.0, a protein band with a molecular weight of about 27 kDa which were not observed in the reference control were clearly observed.

EXAMPLE 20
(Evaluation of Specific-binding Abilities Against E3330)

Two kinds of experiments were conducted to confirm that the proteins with a molecular weight of about 60, 38, and 27 kDa in the nuclear extracts of Jurkat cells were specifically bound to E3330.

The first one was a competitive binding-inhibitory experiment. When in the step of a procedure for the addition of the nuclear extracts to SG-EGDE particles free $NH_2$-E3330 at the same moles of the $NH_2$-E3330 immobilized on the particles or free $NH_2$-E3330 at ten times more moles than the immobilized $NH_2$-E3330 were added simultaneoualy, the protein possessing specifically binding abilities to E3330 immobilized on the. particles would be bound to free $NH_2$-E3330, resulting in a lower yield in the isolation using the particles. As a result, it was confirmed that the yield of the proteins with a molecular weight of about 60, 38, and 27 kDa was lowered, indicating that the proteins were specifically bound to E3330.

Next, the other experiment was conducted by varying the amount of $NH_2$-E3330 Mobilized on the SG-EGDE particles. In the present study the maximum amount of the immobilized E3330 derivatives is 0.4 μmol per 1 mg of SG-EGDE particles. Under these conditions, about 5 to 6 molecules of E3330 derivatives are immobilized on the 1 $mm^2$ of the surface of the particles. This experimental study was conducted in case where the amount of the immobilized E3330' derivatives was 0.2 μmol or 0,4 μmol per 1 mg of SG-EGDE particles. However, in the present invention, amounts of compound immobilized on the particles are varied depending on the properties of the immobilized compounds, conditions of immobilization and so on. The amounts are not defined and are generally varied between a few molecules and hundred molecules. As a result, it was confirmed that the yield of the proteins with a molecular weight of about 60, 38, and 27 kDa increased as the immobilized amount increased. The identification of the specific proteins were conducted by electrophoresis using SDS-PAGE.

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A microsphere comprising a compound possessing physiological activity coupled to a styrene-glycidyl methacrylate polymer through a spacer, wherein the whole surface of the styrene-glycidyl methacrylate polymer is covered with a glycidyl methacrylate.

2. A microsphere according to claim 1, wherein the substance possessing physiological activity is a receptor.

3. A process for isolating a substance that can adhere to a substance possessing physiological activity from a mixture containing the substance, comprising contacting the mixture with a microsphere prepared by coupling the substance possessing physiological activity to a styrene-glycidyl methacrylate polymer through a spacer, wherein the whole surface of the styrene-glycidyl methacrylate polymer is covered with a glycidyl methacrylate, and isolating the substance from the mixture.

4. A process according to claim 3, wherein the substance possessing physiological activity is a receptor.

* * * * *

```
                          SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 1:

Gly Leu Asp Trp Val Lys
 1               5

(2) INFORMATION FOR SEQ ID NO: 2:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 2:

Ala Ala Gly Glu Gly Pro Ala Leu Tyr Glu Asp Pro Pro Asp
 1               5                  10

(2) INFORMATION FOR SEQ ID NO: 3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO
```

(iv) ANTI-SENSE: NO (v) FRAGMENT TYPE: N-terminal (vi) ORIGINAL SOURCE:

(xi) SEQUENCE DESCRIPTION: SEQ ID NO: 3:

```
Gly Ala Val Ala Glu Asp Gly Asp Glu Leu
 1               5                  10
```

(2) INFORMATION FOR SEQ ID NO: 4:

(i) SEQUENCE CHARACTERISTICS:
        (A) LENGTH: 319 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 4:

```
Met Pro Lys Arg Gly Lys Lys Gly Ala Val Ala Glu Asp Gly Asp Glu
 1               5                  10                  15

Leu Arg Thr Glu Pro Glu Ala Lys Lys Ser Lys Thr Ala Ala Lys Lys
                20                  25                  30

Asn Asp Lys Glu Ala Ala Gly Glu Gly Pro Ala Leu Tyr Glu Asp Pro
             35                  40                  45

Pro Asp Gln Lys Thr Ser Pro Ser Gly Lys Pro Ala Thr Leu Lys Ile
         50                  55                  60

Cys Ser Trp Asn Val Asp Gly Leu Arg Ala Trp Ile Lys Lys Lys Gly
 65                  70                  75                  80

Leu Asp Trp Val Lys Glu Glu Asp Ala Pro Asp Ile Leu Cys Leu Gln
                85                  90                  95

Glu Thr Lys Cys Ser Glu Asn Lys Leu Pro Ala Glu Leu Gln Glu Leu
            100                 105                 110

Pro Gly Leu Ser His Gln Tyr Trp Ser Ala Pro Ser Asp Lys Glu Gly
        115                 120                 125

Tyr Ser Gly Val Gly Leu Leu Ser Arg Gln Cys Pro Leu Lys Val Ser
130                 135                 140

Tyr Gly Ile Gly Asp Glu Glu His Asp Gln Glu Gly Arg Val Ile Val
145                 150                 155                 160

Ala Glu Phe Asp Ser Phe Val Leu Val Thr Ala Tyr Val Pro Asn Ala
                165                 170                 175

Gly Arg Gly Leu Val Arg Leu Glu Tyr Arg Gln Arg Trp Asp Glu Ala
            180                 185                 190

Phe Arg Lys Phe Leu Lys Gly Leu Ala Ser Arg Lys Pro Leu Val Leu
        195                 200                 205

Cys Gly Asp Leu Asn Val Ala His Glu Glu Ile Asp Leu Arg Asn Pro
    210                 215                 220

Lys Gly Asn Lys Lys Asn Ala Gly Phe Thr Pro Gln Glu Arg Gln Gly
225                 230                 235                 240

Phe Gly Glu Leu Leu Gln Ala Val Pro Leu Ala Asp Ser Phe Arg His
```

```
                  245                 250                 255
Leu Tyr Pro Asn Thr Pro Tyr Ala Tyr Thr Phe Trp Thr Tyr Met Met
            260                 265                 270

Asn Ala Arg Ser Lys Asn Val Gly Trp Arg Leu Asp Tyr Phe Leu Leu
            275                 280                 285

Ser His Ser Leu Leu Pro Ala Leu Cys Asp Ser Lys Ile Arg Ser Lys
            290                 295                 300

Ala Leu Gly Ser Asp His Cys Pro Ile Thr Leu Tyr Leu Ala Leu
305                 310                 315
```

(2) INFORMATION FOR SEQ ID NO: 5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 5:

GTCTCTCGAG ATGCCGAAGC GTGGGAAAAA G                     31

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 6:

ATGCGGATCC TTACAGTGCT AGGTATAGGG T                     31

(2) INFORMATION FOR SEQ ID NO: 7:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 7:

TAACTAACTA G					11

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 8:

ATTGATTGAT CCTAG					15

(2) INFORMATION FOR SEQ ID NO: 9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 9:

ATGCCTCGAG ATGCCAGCCC TGTATGAGGA CC					32

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 10:

ATGCCTCGAG ATGGATTGGG TAAAGGAAGA AGCC					34

(2) INFORMATION FOR SEQ ID NO: 11:

(i) SEQUENCE CHARACTERISTICS:
        (A) LENGTH: 32 base pairs
        (B) TYPE: nucleic acid

```
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

ATGCCTCGAG ATGCCTTCGG ACAAGGAAGG GT                                          32

(2) INFORMATION FOR SEQ ID NO: 12:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

ATGCCTCGAG ATGTTTGACT CGTTTGTGCT GGTA                                        34

(2) INFORMATION FOR SEQ ID NO: 13:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 13:

Leu Arg Ala Trp Ile Lys Lys Lys Gly Leu Asp Trp Val Lys Glu Glu
 1               5                  10                  15
Ala
```